(12) United States Patent
Mennito et al.

(10) Patent No.: US 9,418,828 B2
(45) Date of Patent: Aug. 16, 2016

(54) CHARACTERIZATION OF PETROLEUM SATURATES

(71) Applicant: ExxonMobil Research and Engineering Company, Annandale, NJ (US)

(72) Inventors: Anthony S. Mennito, Flemington, NJ (US); Kuangnan Qian, Skillman, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 325 days.

(21) Appl. No.: 13/832,564

(22) Filed: Mar. 15, 2013

(65) Prior Publication Data

US 2013/0206980 A1    Aug. 15, 2013

Related U.S. Application Data

(63) Continuation-in-part of application No. 13/716,358, filed on Dec. 17, 2012, and a continuation-in-part of application No. 13/167,816, filed on Jun. 24, 2011, now abandoned.

(60) Provisional application No. 61/423,797, filed on Dec. 16, 2010.

(51) Int. Cl.
*G01N 24/00* (2006.01)
*H01J 49/26* (2006.01)
*G01N 33/28* (2006.01)
*H01J 49/16* (2006.01)

(52) U.S. Cl.
CPC ............ *H01J 49/26* (2013.01); *G01N 33/2835* (2013.01); *H01J 49/164* (2013.01)

(58) Field of Classification Search
None
See application file for complete search history.

(56) References Cited

U.S. PATENT DOCUMENTS

| 4,865,746 | A | * | 9/1989 | Overfield | ..................... 210/656 |
| 6,275,775 | B1 | | 8/2001 | Baco et al. | |
| 7,509,837 | B2 | | 3/2009 | Lubkowitz et al. | |

(Continued)

OTHER PUBLICATIONS

McKay, J. F. et al. High Performance Liquid Chromatographic Separation of Olefin, Saturate, and Aromatic Hydrocarbons in High-Boiling Distillates and Residues of Shale Oil, 1980, Analytical Chemistry, vol. 52, pp. 1618-1621.*

(Continued)

*Primary Examiner* — Robert Xu
(74) *Attorney, Agent, or Firm* — Glenn T. Barrett; Andrew T. Ward

(57) ABSTRACT

A method for characterizing the saturates portion of a petroleum or hydrocarbon sample that includes compounds with boiling points of 1000° F. (538° C.) or higher includes use of laser desorption ionization (LDI) to desorb and vaporize petroleum saturates into the gas phase. After ionization, the saturate compounds cations can be detected using mass spectrometry. The mass spectrum generated from the ionized saturated compounds is then characterized by assigning molecular formulas to any "detected" masses that exhibit a peak with an intensity greater than a defined signal to noise threshold. After making the molecular assignments, the abundance of each assigned molecule can be determined based on the signal magnitude of the peaks in the mass spectrum. The assigned molecules and the corresponding abundances can then be grouped based on a variety of factors.

9 Claims, 15 Drawing Sheets

(56) References Cited

U.S. PATENT DOCUMENTS

2010/0230587 A1     9/2010     Marshall et al.
2013/0206980 A1     8/2013     Mennito et al.

OTHER PUBLICATIONS

Nguyen, H. P., et al. Laser desorption/ionization mass spectrometry fingerprinting of complex hydrocarbon mixtures: application to crude oils using data mining techniques, 2008, Rapid Communications in Mass Spectrometry, vol. 22, pp. 2220-2226.*

T.N. Laremore and R.J. Linhardt, "Improved matrix-assisted laser desorption/ionization mass spectrometric detection of glycosaminoglycan disaccharides as cesium salts", Rapid Communications in Mass Spectrometry, vol. 21, No. 7, Apr. 15, 2007, pp. 1315-1320.

L. Sleno, "The use of mass defect modern mass spectrometry", Journal of Mass Spectrometry, vol. 47, No. 2, Feb. 20, 2012, pp. 226-236.

C.A. Hughey, C.L. Hendrickson, R.P. Rodgers, A.G. Marshall and K. Qian, "Kendrick Mass Defect Spectrum: A Compact Visual Analysis for Ultrahigh-Resolution Broadband Mass Spectra", Analytical Chemistry, vol. 73, No. 19, Oct. 1, 2001, pp. 4676-4681.

PCT Application No. PCT/US2013/072144, Communication from the International Searching Authority, Form PCT/ISA/210, dated Mar. 6, 2014, 13 pages.

Miyabashi et al., "Constituent Analysis of DAO before and after Hydrocracking over Zeolite Catalyst by Ultra-high Resolution Fourier Transform Ion Cyclotrol Resonance Mass Spectrometry", XP-002673940, Proceedings of 15th Saudi-Japan Joint Symposium, Dhahran, Saudi Arabil, Nov. 27-28, 2005, pp. 1-10.

Barman et al., "Petroleum and Coal", XP-002673941, Analytical Chemistry (2001), vol. 73, pp. 2791-2804.

Al-Hajji et al., "Characterization of Nitrogen and Sulfur Compounds in Hydrocracking Feedstocks by Fourier Transform Ion Cyclotron Mass Spectrometry", XP-002673942, Oil & Gas Science and Technology—Rev. IFP, vol. 63, (2008), No. 1, pp. 115-128.

Chen et al., "Laser Desorption Ionization and MALDI Time-of-Flight Mass Spectrometry for Low Molecular Mass Polyethylene Analysis", Journal of the American Society for Mass Spectrometry, vol. 12, pp. 1186-1192 (2001).

* cited by examiner

CHARACTERIZATION OF PETROLEUM SATURATES

CROSS-REFERENCE TO RELATED APPLICATIONS

This application is a continuation-in-part of U.S. application Ser. No. 13/716,358, filed on Dec. 17, 2012, and a continuation-in-part of U.S. application Ser. No. 13/167,816, filed on Jun. 24, 2011, titled "Generation of Model-of-Composition of Petroleum by High Resolution Mass Spectrometry and Associated Analytics, the entirety of which is incorporated by reference, and which claims the benefit of priority of U.S. provisional application No. 61/423,797, which was filed on Dec. 16, 2010.

FIELD OF THE INVENTION

This invention provides methods for characterizing compounds within a petroleum fraction, such as saturate compounds.

BACKGROUND OF THE INVENTION

Petroleum samples are complicated hydrocarbon mixtures containing paraffins, cyclic paraffins (naphthenes), multi-ring aromatics, and various heteroatomic hydrocarbons (most commonly O, S, and N). Virgin petroleum crude oils contain molecules of a wide boiling point range from highly volatile $C_4$ hydrocarbons to nonvolatile asphaltenes. Analysis of petroleum composition of various boiling ranges is valuable for improving the operation of many subsequent processes.

According to at least some conventional definitions, a vacuum gas oil (VGO) is a crude oil fraction that boils between about 343° C. (about 650° F.) to 538° C. (about 1000° F.). A vacuum residuum (VR) is a residuum obtained by vacuum distillation of a crude oil and boils above a temperature about 538° C.

U.S. Pat. No. 6,275,775 describes methods for correlating properties determined by conventional methods with measurements made using a chromatography technique. The described methods start by determining properties for a set of sample compounds using a conventional method, such as using an ASTM method for determining cetane. The reference set of compounds are then characterized using chromatography combined with another spectroscopic technique to characterize the compounds relative to boiling point. The two measurements for the reference compounds are then used to build a model. An unknown sample is then measured using the chromatography and spectroscopic technique, and the model is used to determine the correlated property value for the unknown sample in relation to a predicted boiling point profile for the unknown sample.

An article in the Journal of the American Society for Mass Spectrometry by Chen et al (pg 1186-1192, vol. 12, issue 11, November 2001) describes using matrix assisted laser desorption ionization for generation of ions of polyethylene waxes for detection using mass spectrometry. The article describes use of a copper or cobalt matrix with a silver nitrate solution for forming ions of the wax.

SUMMARY OF THE INVENTION

In an embodiment, a method for characterizing a hydrocarbon sample is provided. The method includes obtaining a hydrocarbon sample comprising at least about 90 wt % of saturate compounds; forming saturate-ion adducts by laser desorption ionization in the presence of a soft Lewis acid; detecting the saturate-ion adducts using mass spectrometry with a resolving power of at least about 10,000, the detected saturate-ion adducts comprising a mass spectrum which is a list of accurate masses and intensities of the corresponding masses; selecting the detected saturate-ion adducts based on Kendrick mass defect values so that Kendrick mass defect values of between about 0.150 to about 0.400 are retained; assigning molecular formula to the selected saturate-ion adducts in the mass spectrum; and determining weight percentages for compounds in the petroleum or hydrocarbon sample based on the intensities of the saturate-ion adducts.

In another embodiment, a method for developing a model of composition for a heavy hydrocarbon sample is provided. The method includes separating a heavy hydrocarbon sample having a T5 boiling point of at least about 350° C. to form a plurality of composition groups, including at least one saturates group; measuring a weight percentage for composition groups formed by separation of the heavy hydrocarbon sample; determining elemental formulas and relative amounts for compounds within separated composition groups using mass spectrometry, the ions for the mass spectrometry being formed using a soft ionization method; and calculating a model of composition for the heavy hydrocarbon sample based on the measured weight percentages for the composition groups, the determined elemental formulas for compounds within the separated composition groups, and the determined relative amounts for compounds within the separated composition groups, wherein the ions for the mass spectrometry of the at least one saturates group are formed using laser desorption ionization.

DETAILED DESCRIPTION OF THE EMBODIMENTS

Overview—Saturates Characterization

Figure 1A:
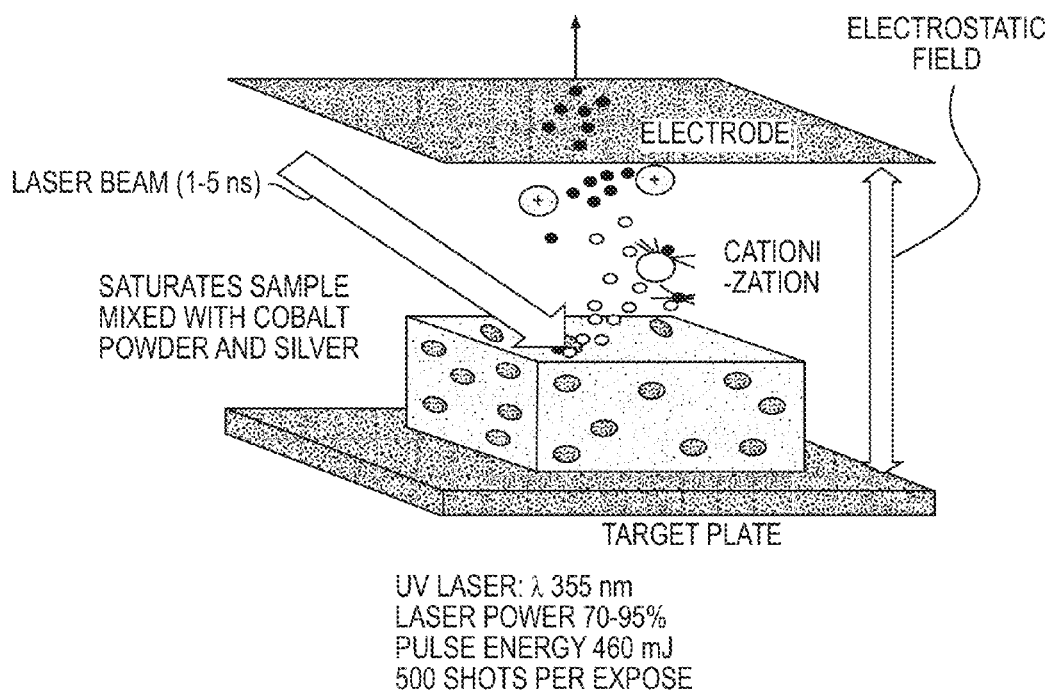
FIG. 1A schematically shows the concept for laser desorption ionization combined with Ag cationization (LDI-Ag).

Petroleum streams are complex mixtures of hydrocarbons containing large numbers of distinct molecular species. Petroleum contains pure hydrocarbons and heteroatom-containing hydrocarbons. Heteroatoms commonly include S, N, O, Ni and V. The terms petroleum and hydrocarbons are used interchangeably in the context of this work. Petroleum streams include, but are not limited to, any hydrocarbon stream from processes that change a petroleum's molecular composition. Particularly, a heavy petroleum refers to the heavier portions of a petroleum fraction, such as the portions of a petroleum fraction corresponding to a vacuum gas oil or a vacuum resid, where the large number of distinct compounds increases the difficulty in accurately characterizing the petroleum fraction. To facilitate chemical and molecular characterization, heavy petroleums are typically separated into fractions of molecules of similar types. A common choice for separation into fractions is to divide a heavy petroleum into saturates, 1-ring aromatics, 2-ring aromatics, 3-ring aromatics, 4-ring+ aromatics, sulfides, polars and/or asphaltenes. Saturates include normal paraffins, isoparaffins, 1-6+ ring cyclic paraffins or naphthenes. VGO naphthenes are mostly 1-6 ring. VR naphthenes could contain 1-14 ring structures. Petroleum saturates are the primary components of lube base oil and petroleum wax. Composition and structure of petroleum saturates have significant implications on the performance properties of finished products. For example, polycyclic ring distribution can greatly affect cold flow properties of a lubricant. High boiling petroleum saturates, e.g. bright stock from resid extraction process, has a high viscosity property because of its high molecular weight. In fuel applications, saturates are considered high value molecules. Currently petroleum saturates are analyzed by field ionization mass spectrometry (FIMS) for VGO molecules or by field desorption ionization mass spectrometry (FDMS) for VR molecules. However, the low ion yields of FDMS and the need to ramp FD emitter temperature during data collection made it difficult to couple FDMS with high resolution MS operation where co-addition of spectra over an extended period of time are needed. Consequently FDMS cannot determine polycyclic ring distribution for the VR molecules.

In various embodiments, a new method to determine composition of petroleum saturates is provided, and in particular petroleum saturates having a boiling point above 538° C. Petroleum saturates are usually a mixture of alkanes (paraffins), as well as cyclic and polycyclic alkanes (naphthenes). The number of cyclic rings ranges from 1 to 6 for VGO molecules and 1-14 for VR molecules. Alkanes can be branched or straight chains (iso or normal paraffins). The method contains the following key components. (1) Separation of petroleum saturates by liquid chromatography (unless the sample is already a saturates fraction generated by refining or other processes). (2) Use of laser desorption ionization (LDI) to desorb and vaporize petroleum saturates into gas phase. (3) Use of soft Lewis acids to form ion complexes with the saturates molecules in the gas phase. (4) Use of high resolution mass spectrometry to determine the exact masses of the formed complex ions. (5) Use of Kendrick mass defects window to remove background noise and ion complex of non-interests. (6) Assign molecular formulas to the masses above a defined signal to noise threshold using a mass tolerance of 0.6 mDa. Only C, H, N, S, O, Ag are allowed. Maximum number of N, S, O are limited to 4. Maximum number of Ag is limited to 1. (7) Determine abundances of molecules based on MS signal magnitude of the corresponding complex ions. (8) Group molecules and their abundances by heteroatom contents, homologous series (Z-number) and molecular weights.

More specifically, in some embodiments laser desorption with Ag ion complexation (LDI-Ag) is used to ionize petroleum VR saturates molecules without fragmentation of the molecular ion structure. Ultra-high resolution Fourier Transform Ion Cyclotron Resonance Mass Spectrometry is applied to determine exact elemental formula of the saturates-Ag cations and corresponding abundances. The saturates fraction composition is arranged by homologous series and molecular weights.

Some embodiments can also include a process of generating MoC of a saturates fraction by reconciling molecular compositions with bulk composition and property measurements, including molecular weight distribution by FDMS, bulk structure measurements by NMR, boiling point distribution by GC, elemental analysis, API gravity, viscosity etc. Petroleum streams are so complex, and have so many distinct molecular species that any molecular approximation of the composition is essentially a model, that is, a model-of-composition (MoC). Detailed analysis of petroleum is necessary for inputs to MoC.

Still other embodiments can also include a process to incorporate a composition of the saturates portion into a MoC of heavy petroleum. The non-saturates petroleum compounds were ionized using atmospheric pressure photon ionization (APPI) and electrospray ionization (ESI). Elemental compositions of molecular ions or pseudo molecular ions were determined by Fourier transform ion cyclotron resonance mass spectrometry. The saturates and non-saturates composition are combined to form a molecular composition of heavy petroleum system Yet other embodiments can further include a process of generating MoC of a heavy petroleum system by reconciling molecular compositions with bulk composition and property measurements. Properties for reconciliation can include molecular weight distribution by FDMS, bulk structure measurements by NMR, boiling point distribution by GC, elemental analysis, API gravity, viscosity etc.

In still other embodiments, an improved method is provided for characterizing the saturates portion of a petroleum or hydrocarbon sample that includes compounds with boiling points of 1000° F. (538° C.) or higher. The method includes use of laser desorption ionization (LDI) to desorb and vaporize petroleum saturates into the gas phase. The ionization can be facilitated by use of soft Lewis acids, such as Ag cation, to form saturates-Ag cation complexes with the saturates molecules that are desorbed and vaporized in the gas phase. After ionization, the saturate compounds cations can be detected using mass spectrometry. Preferably, a high resolution mass spectrometry is used that allows for distinction between formed complex ions that have different molecular compositions but similar masses, such as distinguishing between the mass of a nitrogen atom versus a $^{13}CH$ group, or distinguishing between $CH_4$ versus O. The mass spectrum generated from the ionized saturated compounds is then characterized by assigning molecular formulas to any "detected" masses that exhibit a peak with an intensity greater than a defined signal to noise threshold. After making the molecular assignments, the abundance of each assigned molecule can be determined based on the signal magnitude of the peaks in the mass spectrum. The assigned molecules and the corresponding abundances can then be grouped based on a variety of factors, such heteroatom content, homologous series (Z-number), and/or molecular weights.

In this description, reference will be made to hydrocarbon streams or hydrocarbon mixtures. As noted above, hydrocarbon streams or mixtures are defined herein to include streams or mixtures containing heteroatoms. As understood by those of skill in the art, a typical mineral petroleum feedstock often includes compounds containing heteroatoms, such as (but not limited to) compounds containing sulfur, nitrogen, trace metals, and/or oxygen. Unless it is specifically indicated otherwise, hydrocarbon streams or hydrocarbon mixtures are defined to include streams or mixtures containing compounds that include such heteroatoms.

Hydrocarbons (including compounds containing a heteroatom) within a petroleum fraction that have a boiling point of 1000° F. (538° C.) or greater can pose particular challenges during characterization. These hydrocarbon compounds are often referred to as the "bottoms of the barrel" as they cannot be distilled via conventional vacuum distillation tower. A more common name of this non-distillable fraction is vacuum residua or vacuum resid (VR). Relative to a vacuum gas oils (VGO), vacuum resids exhibit distinct chemical and physical characteristics.

Compounds with boiling points above 1000° F. present a difficult analytical challenge in comparison with lower boiling compounds, especially in the area of molecular level characterization. Some challenges for such compounds are related to the high boiling points and corresponding high molecular weights. Nominally, the boiling points of vacuum resid molecules are above 1000° F. Molecular weights for vacuum resid molecules may range from 300 Da to 3000 Da (versus 100 to 800 Da for vacuum gas oil molecules). The high molecular weights of vacuum resids arise from both alkyl chain extension ($CH_2$ increments) and polyaromatic ring growth. Traditional thermal vaporization and ionization methods are inefficient to convert vacuum resid molecules into intact molecular ions for detection. Other challenges are related to low solubility of at least some compounds in a vacuum resid fraction. Vacuum resids typically contain asphaltenes (defined as n-heptane insolubles in this work). The range of asphaltenes content is from 0 to 40%. The low solubility and high asphaltenes contents of vacuum resids largely arise from the rich heteroatom content (N, S, O) and low H/C ratios of such fractions. Still other challenges are related to the large number of molecules in vacuum resid (50 to 100 times more than that in vacuum gas oil in terms of mass distinguishable species) and significant increases in nitrogen, sulfur, oxygen, and metal heteroatom contributions. Mass spectrometry performance needs to be maximized in terms of mass resolution, mass accuracy and dynamic range to account for all molecules in a vacuum resid. Finally, vacuum resid molecules are likely to contain multi-core structures (versus mostly single cores in vacuum gas oil), making structure assignment difficult.

An additional difficulty in characterizing a vacuum resid fraction is that different types of compounds within the fraction respond differently to characterization techniques. Some compounds within a vacuum resid fraction, such as aromatic and polar compounds, can be studied in a relatively straightforward manner using mass spectrometry. Saturate compounds within a vacuum resid fraction, however, pose additional challenges. One option for characterizing petroleum saturates is to use field ionization mass spectrometry (FIMS) for 1000° F.− molecules and to use field desorption ionization mass spectrometry (FDMS) for 1000° F.+ molecules. However, the low ion yields of FDMS and the need to ramp the field desorption emitter temperature during data collection makes it difficult to couple FDMS with high resolution mass spectrometry operation, due in part to the need for co-addition of spectra over an extended period of time. Consequently FDMS cannot determine polycyclic ring distribution for 1000° F.+ saturate molecules.

Atmospheric pressure photoionization (APPI), atmospheric pressure chemical ionization (APCI), and electrospray ionization (ESI) are not effective for ionizing petroleum saturates because of the lack of a charging site on the saturate molecules. APPI is the preferred ionization method for petroleum aromatics. ESI is the preferred ionization method for petroleum polars.

Heavy Saturates Fractions for Analysis

In various embodiments, the methods described herein are suitable for detailed characterization of the saturates portion of a petroleum feed, such as the saturates portion of a heavy hydrocarbon sample. A heavy hydrocarbon sample can be a sample from one or more feedstocks, products, and/or intermediate feeds or products that correspond to a heavy hydrocarbon fraction. Unless otherwise specified, a heavy hydrocarbon fraction, sample, feedstock, or product is defined herein to include fractions, samples, feedstocks, or products that include heteroatoms other than carbon and hydrogen (such as sulfur, nitrogen, oxygen, or metals). Unless otherwise specified, a reference to a heavy hydrocarbon sample represents a portion of a heavy hydrocarbon fraction, feedstock, product, or other heavy hydrocarbon source that is used in order to characterize the properties of the heavy hydrocarbon source.

In some aspects, a heavy hydrocarbon sample (and therefore the heavy hydrocarbon source the sample is derived from) corresponds to a vacuum gas oil, a vacuum resid, or a combination thereof. Another way of determining whether a sample corresponds to a heavy hydrocarbon is based on boiling point. For a heavy hydrocarbon sample based on a vacuum gas oil feed, the sample can have an initial boiling point of at least about 343° C., a T5 boiling point of at least about 343° C., or a T10 boiling point of at least about 343° C. A reference to a "Tx" boiling point corresponds to a temperature where "x" weight percent of a sample will boil. The boiling point profile for a heavy hydrocarbon can be determined by a suitable ASTM distillation method, such as ASTM D86.

In other aspects, a heavy hydrocarbon sample can have an initial boiling point of at least about 375° C., or a T5 boiling point of at least about 375° C., or a T10 boiling point of at least about 375° C. In still other aspects, a heavy hydrocarbon sample can have an initial boiling point of at least about 400° C., or a T5 boiling point of at least about 400° C., or a T10 boiling point of at least about 400° C. These higher boiling range specifications for the heavy hydrocarbon sample are preferable in some embodiments, as these higher boiling range samples may be better characterized using the techniques described herein. In particular, lower boiling range saturates pose some difficulties in characterization. Characterization of lower boiling points saturates can be done using Field Ionization mass spectrometry.

Some petroleum streams, such as wax, certain lube base oil and bright stocks, contains >90% of petroleum saturates. These materials may be directly characterized by the method without further fractionation.

For characterization of a saturates portion or sample, if the sample does not already correspond to a saturates portion, the saturates portion can be separated from the petroleum sample, such as a heavy hydrocarbon sample. Liquid chromatography is a suitable method for separating the saturates portion of a sample from other types of compounds in a sample. A saturates portion, fraction, or sample is defined as a sample that comprises at least about 90 wt % of saturate compounds, such as at least about 95 wt % of saturate compounds, and preferably at least about 98 wt % of saturate compounds.

In some embodiments, the saturates portion corresponds to saturates from a heavy hydrocarbon sample. Preferably, the saturates portion of such a sample has an initial boiling point of at least about 343° C., such as at least about 375° C. or at least about 400° C.; and/or a T5 boiling point of at least about 343° C., such as at least about 375° C. or at least about 400° C.; and/or a T10 boiling point of at least about 343° C., such as at least about 375° C. or at least about 400° C.

In other embodiments, the saturates portion for characterization can correspond to a saturates portion with an initial boiling point of at least about 950° F. (510° C.), such as at least about 975° F. (524° C.) or at least about 1000° F. (538° C.). This corresponds to a saturates portion that poses additional challenges, due to the difficulties in forming a vapor phase molecular ion or pseudo molecular ion that can be characterized using mass spectrometry. Still another option for characterizing a saturates portion is based on the molecular weight distribution of the saturates portion. Preferably, about 10 wt % or less of the saturates portion has a molecular weight of 400 Daltons or less, such as about 5 wt % or less.

Laser Desorption Ionization and Cation Complex Formation

Laser desorption ionization has previously been used to desorb non-volatile molecules into the gas phase. The gas phase sample molecules can be subsequently ionized via protonation or charge transfer. In laser desorption ionization, localized intense heating caused rapid vaporization of analyte molecules. Fragmentation is usually reduced or minimized relative to other methods of desorption for high boiling point molecules, especially for aromatic-containing molecules. However, saturate molecules have a relatively high susceptibility for fragmentation during laser desorption ionization.

Although petroleum saturates can be desorbed using direct laser desorption ionization, it has been found that addition of various other components can improve the effectiveness of a laser desorption ionization technique. One type of component that can be added is a component that can form an ion adduct or complex with the saturate molecule. Direct ionization of petroleum saturates by laser desorption ionization is typically inefficient. Additionally, forming an ion directly from a saturate molecule tends to also result in a substantial amount of molecular ion fragmentation. To overcome this difficulty, a soft Lewis acid can be added to the saturate sample and/or present during desorption to assist with ion formation. Silver ions ($Ag^+$) are an example of a suitable soft Lewis acid that can form an ion complex with a saturate molecule. Instead of ionizing the saturate molecule, a saturate molecule and silver ion adduct can be formed, so that the silver ion accommodates the ionic charge. This results in a substantially lower fragmentation rate for the saturate compounds as compared to forcing the saturate compounds to directly carry the ionic charge (such as in high energy electron impact ionization). It is believed that other soft Lewis acids may serve the same purpose as silver cations. Other examples of suitable soft Lewis acids include various noble metal ions, as well as some additional transition metal ions. Examples of suitable soft Lewis acids in a "+1" oxidation state include $Cu^+$, $Ag^+$, $Au^+$, $Tl^+$, and $Cs^+$. Examples of suitable soft Lewis acids in a "+2" oxidation state include $Pd^{2+}$, $Pt^{2+}$, $Cd^{2+}$, and $Hg^{2+}$. It is noted that organometallics containing an appropriate soft Lewis acid ion may also be suitable, such as $CH_3Hg^+$. $Tl^{3+}$ may also be suitable, as well as $Tl(CH_3)_3$.

Another additional type of component is a component that provides a matrix that can facilitate desorption, vaporization, and/or ionization. Cobalt powder is an example of a suitable matrix material that improves the efficiency of desorption or vaporization. One hypothesis is that cobalt powders absorb heat efficiently and serve as a heat transfer vehicle. A suitable powder size for the cobalt powder is from about 5 μm to about 100 μm, such as about 30 μm.

Another potential type of matrix compound is an organic acid, such as 2, 5 dihydroxybenzoic acid. Having an organic acid present during laser desorption ionization can assist with ionization of a sample. An organic acid can be used separately from or in combination with a cobalt powder matrix.

It is noted that aromatic molecules have higher tendency to form ion-molecule adducts or complexes with Ag and/or other soft Lewis acids. As a result, separation of saturate compounds from any aromatic or polar compounds in a same is beneficial in order to avoid preferential desorption and ionization of the aromatic molecules and/or polar molecules.

Unless otherwise specified, for the saturates portions analyzed by mass spectrometry, a saturates sample was initially prepared using the following procedure. Fine cobalt powder (30 um in diameter) was dissolved in isopropanol to form a slurry with a concentration of 150 mg Co/ml. Saturated silver nitrate in ethanol was prepared by dissolving at least 31 g of silver nitrate in 1000 g of 190 proof ethanol. About 25 mg/ml of a saturates sample was diluted in toluene. Sets of three ~1-ul aliquots of the cobalt slurry were deposited on a target plate for laser desorption ionization. Two-three 1-ul aliquots of a 1:1 ratio of silver nitrate and saturates sample solution were deposited on the dried cobalt bed. Once the deposited sample mixture was dried, the target plate was inserted into the mass spectrometer source area and desorbed using a UV laser.

The following is an example of how soft ionization of a sample or a portion of a sample, such as a saturates portion separated out using high pressure liquid chromatography, can be performed using laser desorption ionization. FIG. 1A shows the concept for the matrix assisted laser desorption ionization (MALDI)—Co—Ag FTICR MS measurements described herein. Fine cobalt powder (30 μm in diameter from Aldrich) is dissolved in isopropanol to form a slurry with a concentration of 150 mg/ml. Saturated silver nitrate (from Sigma) in ethanol is prepared by dissolving >31 g of silver nitrate in 1000 g of 190 proof ethanol [from Aaper]. For samples that were investigated using MALDI FTICR MS, about 25 mg/ml of the sample was diluted in toluene. This includes either standard samples, such as polyethylene waxes, or petroleum saturates samples. Sets of three (approximately) 1 μl aliquots of the cobalt slurry were deposited on the MALDI target plate. Typically, a 1:1 ratio of silver nitrate and sample were then mixed and deposited on the dried cobalt bed. Once the deposited sample mixture was dried, the target plate was inserted into the mass spec source area and desorbed using a UV laser.

Determination of Elemental Formula and Abundances of Molecular Ions by Mass Spectrometry In various embodiments, a method is provided for characterizing a saturates portion derived from a petroleum sample (such as a heavy hydrocarbon sample) using high resolution mass spectrometry and associated analytical techniques. Conventionally, a magnetic sector mass spectrometer has been used to determine petroleum composition. In general, however, a sector mass spectrometer provides limited mass resolution. A resolution power of 10K to 50K can be normally achieved when used in electron ionization (EI) mode and 1K to 5K when used in Field Ionization (FI) mode. More recently time of flight (TOF) mass spectrometry with a resolution power of around 5K in conjunction with FI has been used to determine petroleum compositions of VGO range molecules. Unfortunately, EI produces too much fragmentation during the ionization process and cannot be used to determine molecular ion composition. The low mass resolution in FI mode prohibits resolutions of many overlapping masses in petroleum. This creates difficulties when attempting to make unique assignments of molecular formula for the molecular ions.

In various embodiments, petroleum samples are analyzed by high resolution mass spectrometry (HRMS) to resolve or partially resolve nominal mass overlap in the samples. Mass resolution here is defined as $R=M/\Delta M_{FWHM}$ where $\Delta M_{FWHM}$ is defined as mass peak width at 50% peak height. Mass resolving power (RP) and mass resolution are used interchangeably in this work. A minimum mass resolution of 10,000 is needed to resolve important overlaps, such as the distinction between the mass of 12 hydrogen atoms versus the mass of a carbon atom. Preferably, the mass resolution can be at least 50,000, such as at least 65,000, in order to resolve $^{107}Ag\,H_2$ versus $^{109}Ag$. The mass difference between the pair is about 16 mDa. More preferably, Fourier transfer ion cyclotron resonance mass spectrometry is used with a mass resolution ($R=M/\Delta M_{FWHM}$) of greater than 100,000 to resolve overlapping masses, such as, $^{12}C_2H_2$ versus $^{13}C_2$, and $^{13}C_2\,^{107}Ag$ versus $^{12}C_2\,^{109}Ag$. The mass differences of the two pairs are 8.9 and 7.0 mDa, respectively The laser desorption ionization apparatus used to obtain the results provided herein is an example of a suitable laser desorption apparatus. The laser desorption ionization results described herein were collected using a Bruker Apex-Qe FTICR Apollo II Source with matrix assisted laser desorption capability. The laser source was a NG/YAG Laser with a wavelength of 355 nm. Laser power was controlled between 70-95% of a maximum pulse energy of 460 mJ. During data collection, 500 shots per exposure were performed and high resolution data were co-added into one spectrum. The FTICR-MS conditions were fine-tuned for molecular mass range of interests. The laser plate was set to 300 V to push ions from plate into ion funnels that lead to a FTICR cell for mass analysis.

In the examples provided herein, data are typically collected in a broadband acquisition mode (a mass range of 300 Da to 3000 Da). Preferably, Fourier transform ion cyclotron resonance mass spectrometry (FTICR-MS) with an average mass resolving power (RP>300K) is utilized for the analysis. FTICR-MS allows for resolution and determination of masses with high accuracy (error<0.2 ppm). Concentrations of the masses were determined by the signal magnitude of corresponding masses. Empirical formulas can be determined without ambiguity within the accuracy of mass analysis window and restrictions of heteroatom combinations. Chromatographic separation may be used to form a saturates portion for analysis by separating saturates from other compounds in a petroleum sample. Molecular structure assignments are made based on empirical formula. At the end, composition may be reconciled so that average composition and properties are consistent with that measured by bulk measurement technologies, such as NMR and elemental analysis.

In FTICR MS, the excited cyclotron motion of the ions is detected on receiver plates as a time domain signal that contains all the cyclotron frequencies that have been excited. Fourier transformation of the time domain signal results in the frequency domain signal that can be converted into a mass spectrum. In this work, the mass range was set at m/z 300 to 3000, and the dataset size was set to 4 Megawords. Ion accumulation time was 0.5 to 2 sec. 1000 data sets were co-added to generate the final spectrum. Bruker Data Analysis (DA) software is used to find the mass peak list with signal-to-noise ratio (S/N) greater than 6. The mass peak list is further analyzed for identification of hydrocarbon molecules. External mass calibration was performed using a blend of eight in-house synthesized aromatic compounds covering a mass range from about 350 to 1800 Da. In general, 2 ppm mass accuracy can be achieved with external calibration. Bruker DA molecular formula tool assisted in identifying major homologous series. Internal calibration was then performed using the identified homologous series. On average, about 0.2 ppm mass accuracy can be achieved with internal mass calibration FTICR MS provides three layers of chemical information for a petroleum system. The first level is heteroatomic classes (or compound classes), such as hydrocarbons (HC), 1 sulfur molecules (1S), 1 nitrogen molecules (1N), 2 oxygen molecules (2O), 1 nitrogen 1 oxygen molecules (1N1O), etc. The second level is Z-number distribution (or homologous series distribution) within each compound class. Z is defined as hydrogen deficiency as in general chemical formula, $C_cH_{2c+z}N_nS_sO_o$. The more negative the Z-number, the more unsaturated the molecules. The third level of information is the total carbon number distribution or molecular weight distribution of each homolog. If compound core structure is known, total alkyl side chain information can be derived by subtracting carbon number of cores.

Petroleum saturates contain minimum amount of heteroatoms, such as S, N, O. Some oxygenates can be formed in ionization step due to oxidation. In general, for 1000F− molecules, Z-span ranges from 2 to −12 with increment interval of 2. The corresponding structures are non-cyclic alkanes, 1 to 6 ring naphthenes. For 1000F+ molecules, Z-span can range from 2 to −24, corresponding to alkanes and 1 to 12 ring naphthenes.

Preferably, the molecular formula of detected saturate compounds are assigned for mass peaks having greater than a threshold level of signal-to-noise ratio using a mass tolerance of 0.6 mDa. Preferably, the assignments are made by assuming that only C, H, N, S, O, and Ag atoms are present in the detected ions. During assignment of the molecular formula, the number of certain types of atoms, such as N, S, and O, can be limited to a maximum number per atom. For example, the number N atoms, S atoms, and O atoms within a compound can each be limited to 4 or less. Similarly, the maximum number of Ag atoms can be limited to 1.

Examples of Saturates Analysis

Figure 2:
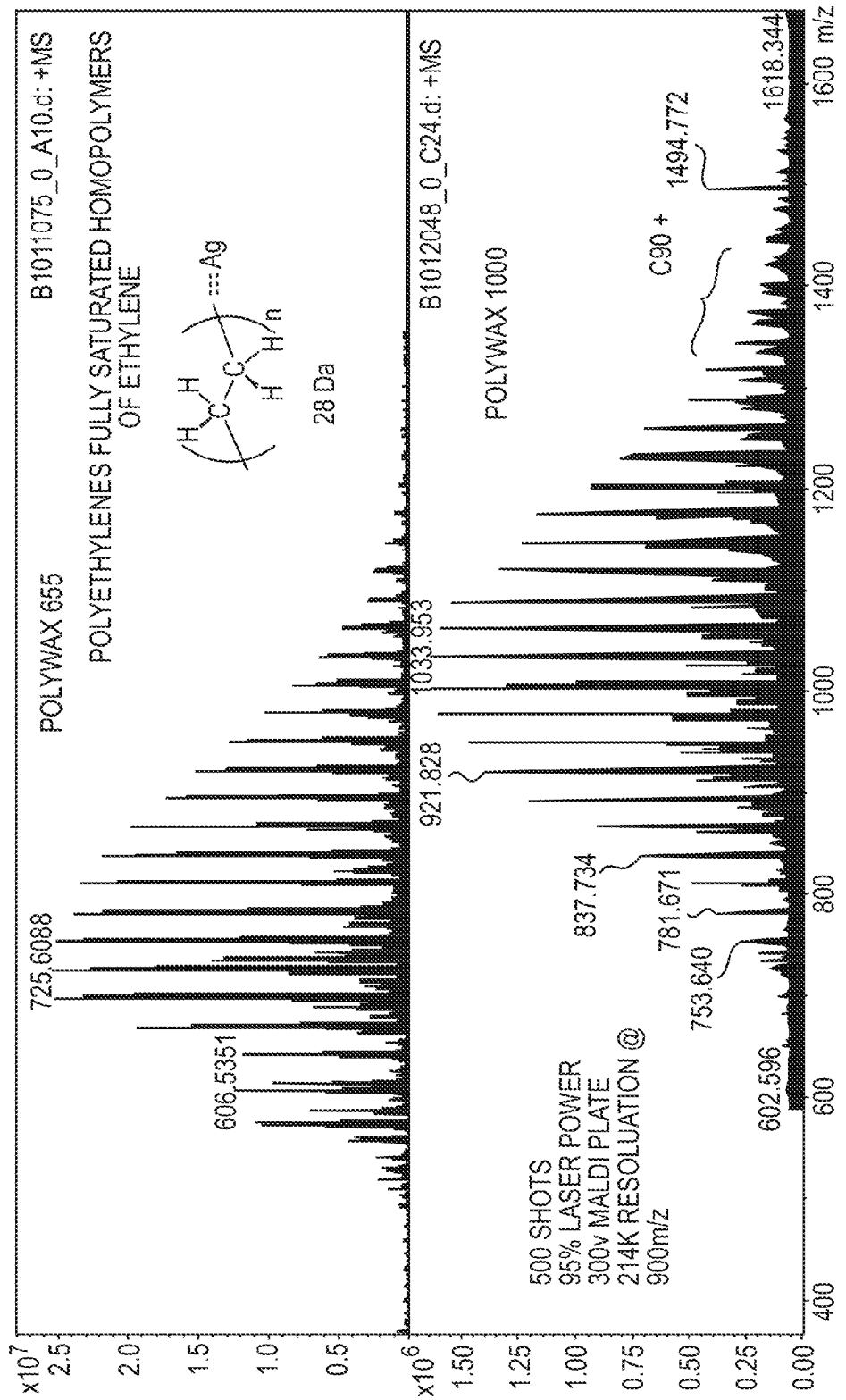
FIG. 2 shows mass spectra of polywax 655 and polywax 1000 by LDI-Ag.

A variety of samples were studied to verify the suitability of FTICR-MS for characterization of saturates samples. One application was to study Polywax 655 and 1000. Polywax 655 and 1000 are fully saturated homopolymers of ehylene with distributions at various molecular weights. Since Polywax 655 and 1000 are mostly paraffin molecules, mass spectra were obtained with little or no interference from other classes of molecules. Commercial Polywax 655 and 1000 standards have a carbon number span of 30 to 80 and 45 to 100, respectively. Results of the analyses of the Polywax 655 and 1000 samples are shown in FIG. 2. Average molecular weights for the two polymers are consistent with the commercial specifications for Polywax 655 and 1000, respectively. Due to the high resolution of the FTICR-MS technique, the amount of baseline increase in the mass spectra is low (indicating the lack of mass overlaps due to insufficient mass resolution), which facilitates determination of the relative weights of the various saturate species in the sample.

Figure 1B:
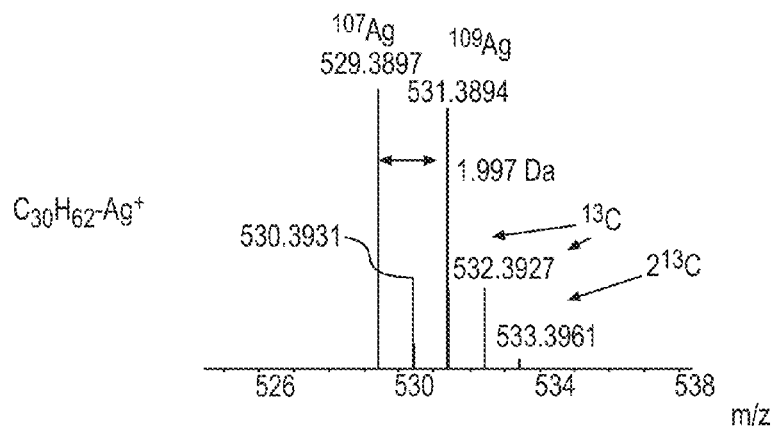
FIG. 1B shows an example of resolving peaks due to different silver ion isotopes in a mass spectrum of C30 alkane.
Figure 3:
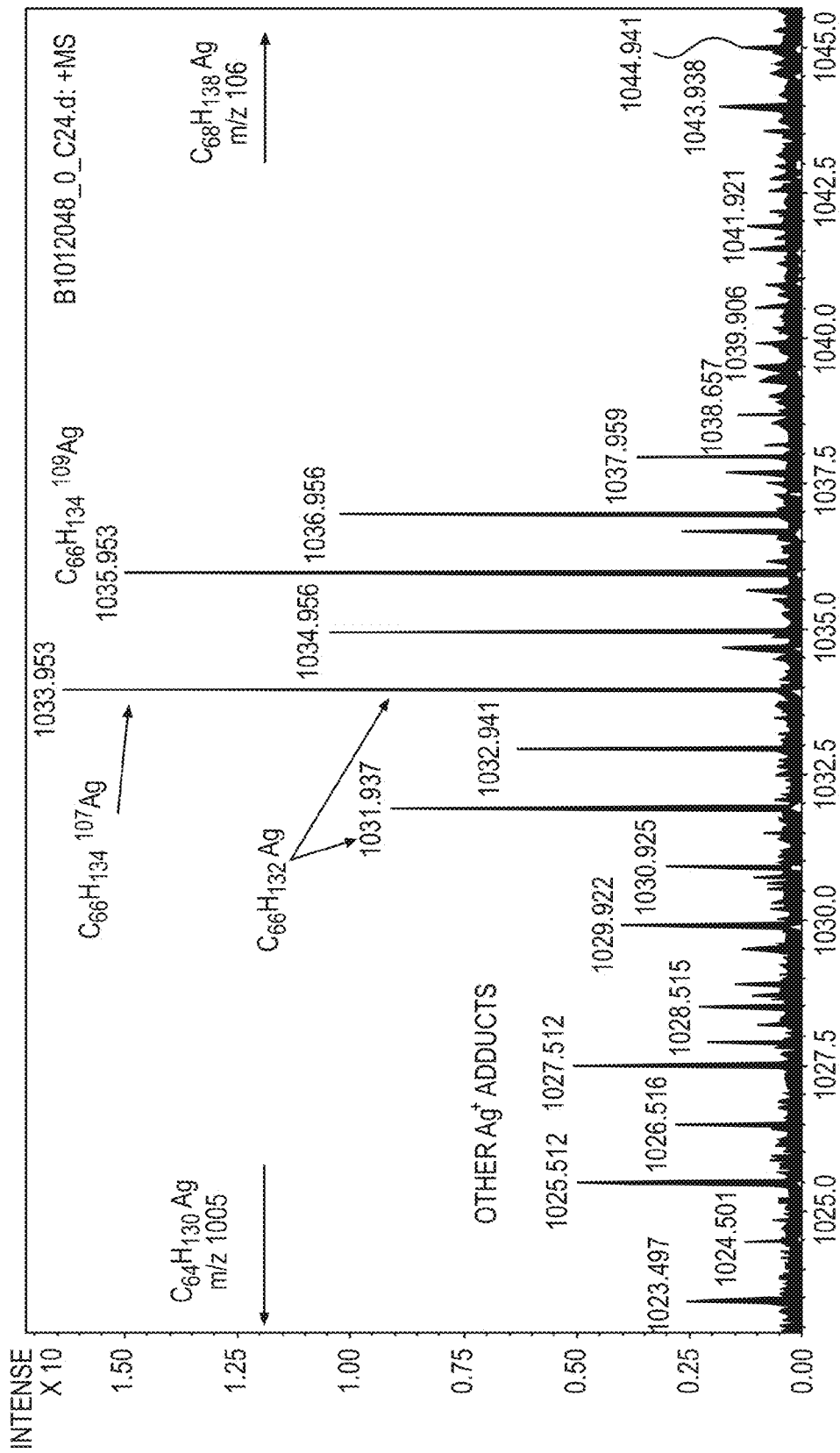
FIG. 3 shows a segment (m/z 1023 to 1046) of mass spectrum of polywax 1000. An example of ionization of C66 alkane.

FIG. 3 shows a zoom-in mass spectrum at m/z 1033 for one of the Polywax samples. As shown in FIG. 3, the high resolution mass spectrometry used for characterization allows for positive identification of the various types of Ag adducts formed with the saturate hydrocarbon species. For example, FIG. 3 shows that for most compounds, the mass peaks actually appear as a pair of peaks with a mass difference of about 2 Da. This is due to roughly equal isotope concentrations of $^{107}$Ag and $^{109}$Ag. However, the difference in mass for an alkane and an alkene corresponds to two hydrogen atoms, so the difference in mass between an alkane and an alkene is also about 2 Da. In order to resolve the 16.0 mDa difference between, for example $C_{66}H_{132}+^{109}Ag$ and $C_{66}H_{134}+^{107}Ag$, requires a mass resolving power of 65,000. FIG. 1B shows a similar resolution of the distinction between Ag adducts.

The differentiation provided by high resolution mass spectrometry also allows for exclusion of peaks due to complexes or adducts that involve more than just a single Ag+ ion. Other adducts that may be formed during laser desorption ionization include, for example, $[Ag_2NO_3]^+$, $[Ag_3(NO_3)_2]^+$ Preferably, mass peaks corresponding to these adducts with two or more Ag atoms can be identified so as to simplify analysis of the mass spectrum.

One convenient way of identifying such adducts with larger numbers of Ag atoms is via a Kendrick mass defect analysis. A standard IUPAC mass scale defines the mass of a $^{12}$C atom to be exactly 12 Da. However, in a hydrocarbon sample, the most common grouping of atoms is a $CH_2$ unit. In order to identify hydrocarbon homologues, a revised mass scale can be used so that the mass of a $CH_2$ unit is defined to be exactly 14. This can be accomplished by multiplying the IUPAC mass for a compound by the factor 14/14.01565.

After adjusting the molecular weight using the Kendrick scale where a $CH_2$ unit weighs exactly 14, the Kendrick mass defect for each peak in the spectrum can be calculated. The Kendrick mass defect (KMD) is defined by equation (1).

$$KMD = (\text{nominal mass} - \text{Kendrick mass}) \quad (1)$$

In equation 1, the differences between the nominal mass and the Kendrick mass based on carbon or hydrogen atoms will be small for petroleum saturates, even for a molecule with up to 100 carbon atoms. As a result, a Kendrick mass defect of more than about 0.200 will be due to the presence of heteroatoms. Additionally, in a plot of Kendrick mass defect versus Kendrick mass, compounds that are homologues with the same heteroatoms should be aligned.

Figure 4:
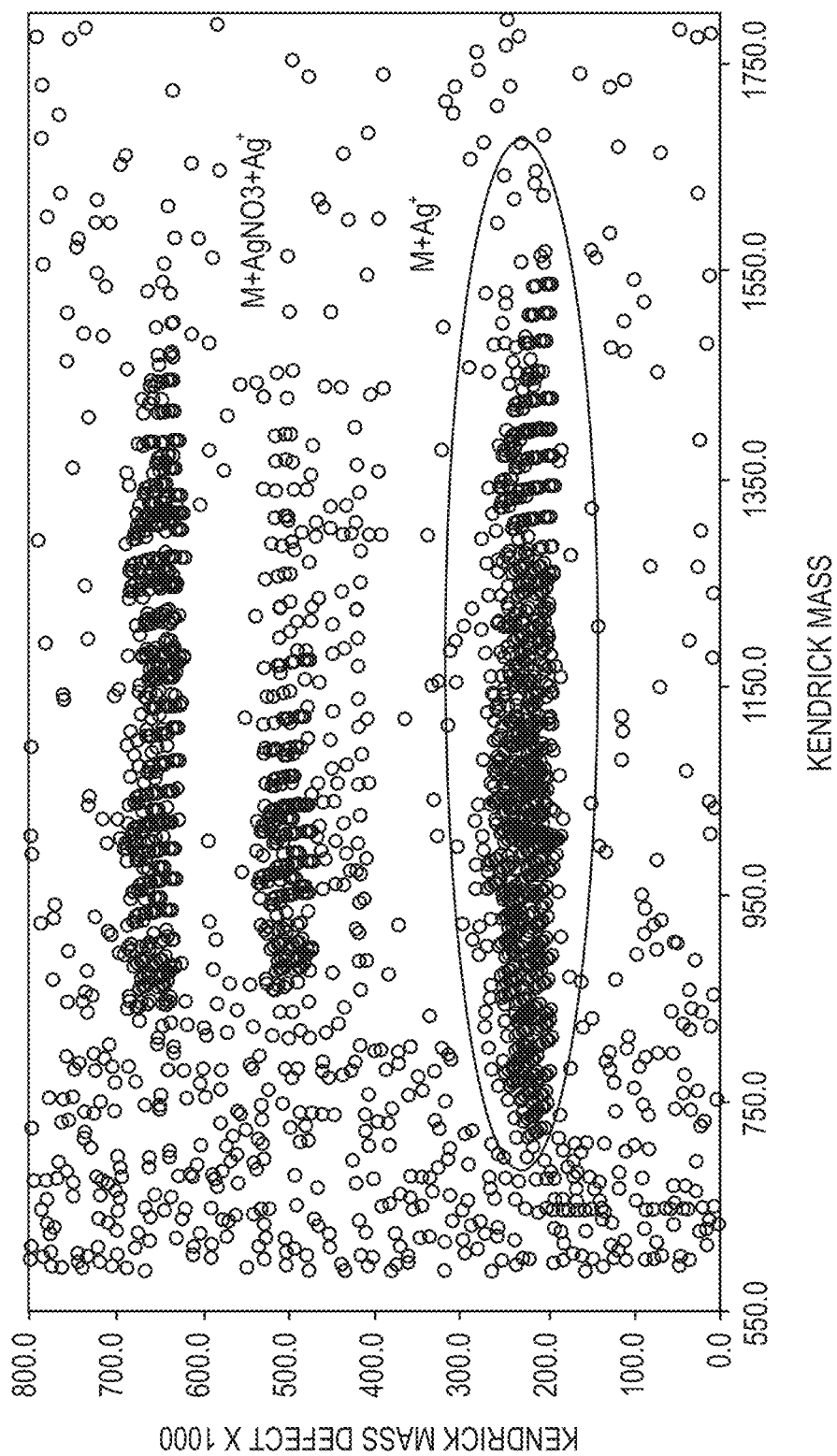
FIG. 4 shows an example of a Kendrick mass defect (KMD) plot. KMD is multiplied by 1000 in y-axis.

FIG. 4 shows the Kendrick mass defect plot of Polywax 1000. As shown in FIG. 4, compounds with multiple silver atoms in the saturate complex are aligned, such as the alignment of compounds with just one silver atom between 0.200 and 0.300. By contrast, compounds with two silver atoms are aligned at a Kendrick defect mass number closer to 0.500. By selecting a Kendrick mass defect window of 0.200 to 0.300, compounds with unwanted masses can be efficiently removed, thus simplifying analysis of the mass spectra.

Figure 5:
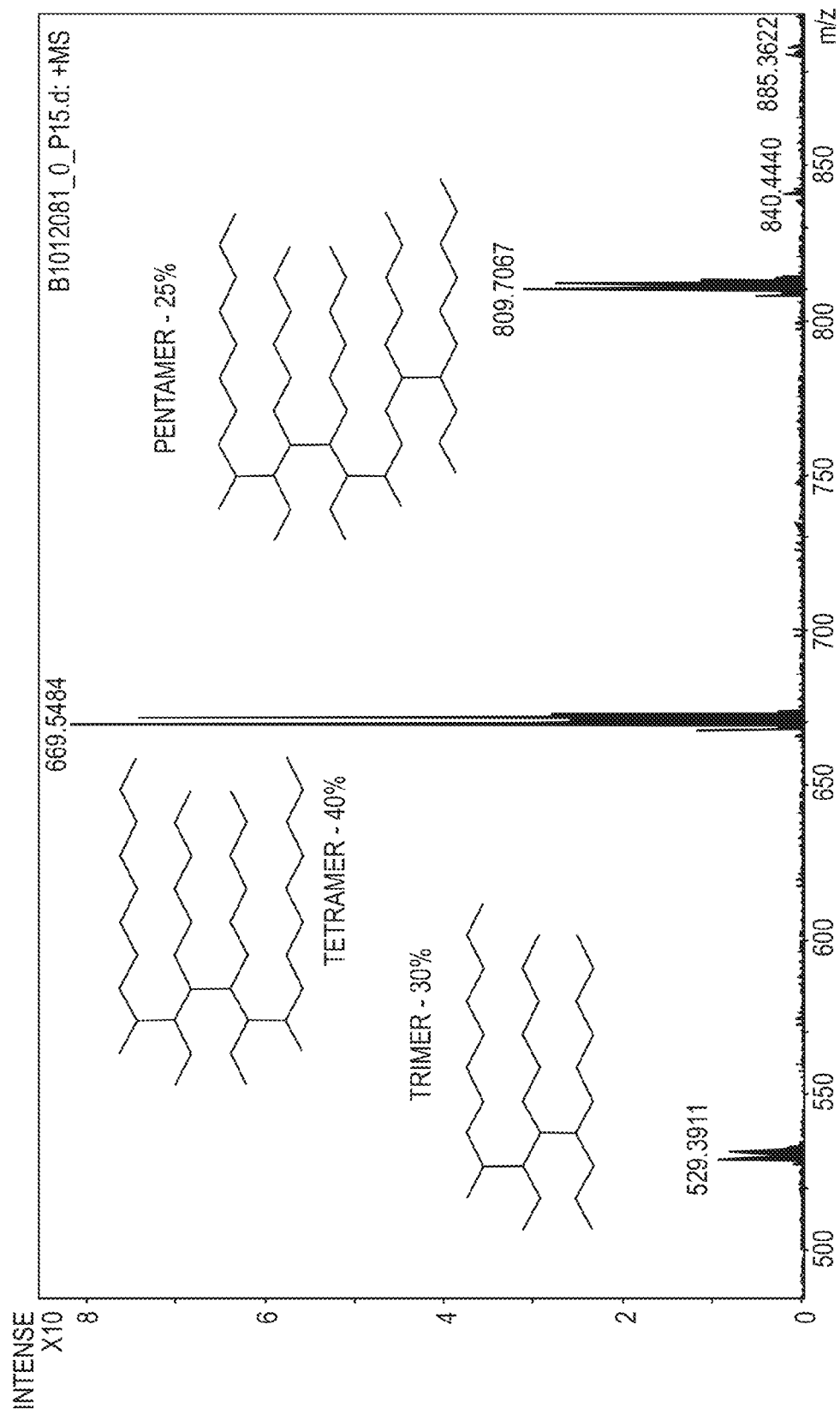
FIG. 5 shows mass spectra for poly alpha olefin 6.

As another example of characterization a saturate sample, the synthetic lubricant poly-alpha-olefin 6 was analyzed. FIG. 5 shows the mass spectrum of PAO 6 by the technique. Ag adducts of C30, C40 and C50 poly-alpha-olefins are all observed. Although not shown in FIG. 5, we observed [(M−2)+Ag]$^+$ ion in addition to [M+Ag]$^+$. The level of [M−2+Ag]$^+$ relative to [M+Ag]$^+$ was about 1:10.

Figure 6A:
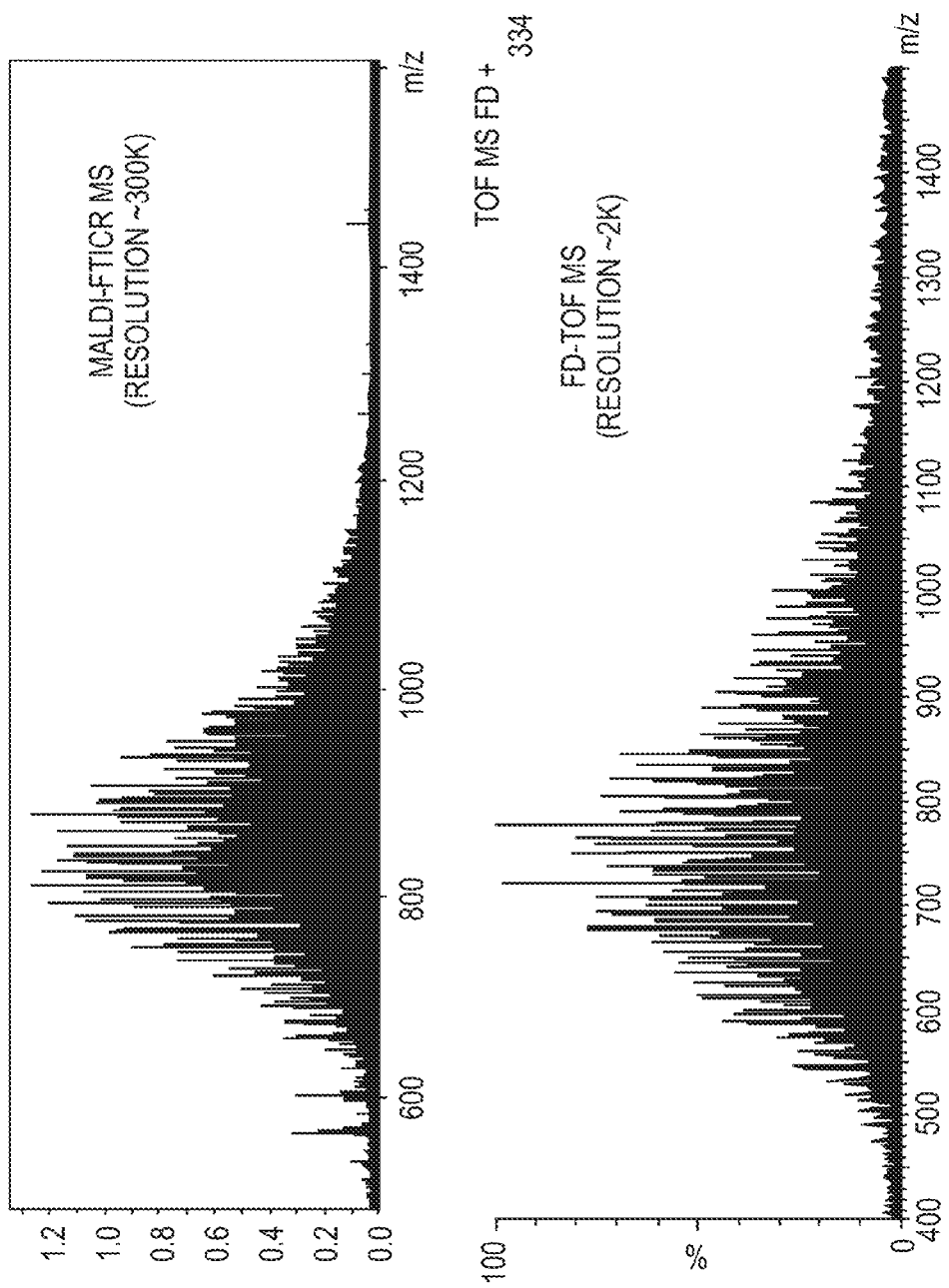
FIG. 6A compares broadband mass spectra of a vacuum resid (VR) obtained by LDI-Ag versus that obtained by field desorption low resolution mass spectrometry.

As still another example, a saturates portion isolated from a vacuum resid sample was analyzed for comparison by both laser desorption ionization FTICR-MS and by low resolution field desorption time-of-flight mass spectrometry (FDMS). FIG. 6 compares the mass spectra of a VR obtained by the two techniques. The two mass spectra are offset from one another by roughly 100 g/mol, which roughly corresponds to the mass of an Ag ion (~108 g/mol). Molecules with molecular weight of 500 to 1300 g/mol were observed in the laser desorption ionization FTICR-MS mass spectrum, which corresponds to molecules with neutral molecular weight of 400 to 1200 g/mol as shown in the FDMS mass spectrum. Similarly, the center of the laser desorption ionization FTICR-MS is around 850 while that of field desorption time-of-flight MS is around 750. As shown in FIG. 6A, the laser desorption ionization method produces a spectrum with a similar shape in comparison with the field desorption time-of-flight MS. However, the laser desorption ionization method coupled with FTICR-MS provides a resolving power of about 300,000, as compared to a resolving power of about 2000 for field desorption time-of-flight MS.

Figure 6B:
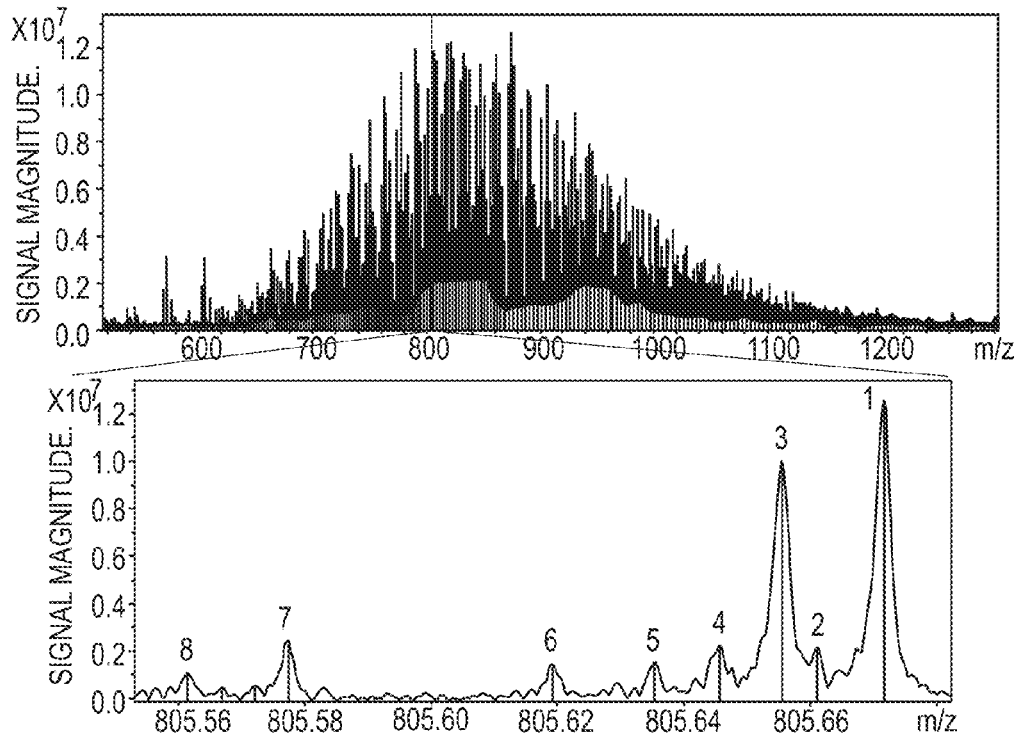
FIG. 6B shows broad band mass spectrum (m/z 500 to 1300) of the VR in FIG. 6A (top) and a segment of the mass spectrum (m/z 805.5 to 805.7), and assignments of elemental formula of mass peaks in the mass spectrum segment.

High resolution mass spectrometry is preferred for characterization of saturates. FIG. 6B shows a full mass spectra and zoom-in mass spectrum at a mass to charge ratio (m/z) of ~805. A total of 8 components were mass resolved and positively identified with a nominal mass of 805. The mass difference between peak 1 and 3 is 16 mD ($^{109}$Ag/H$_2$$^{107}$Ag) which needs a mass resolving power (RP=M/$\Delta M_{FWHM}$) of ~50K for separation. The mass difference between peak 2 and 3 is 7 mDa which needs a mass resolving power of 110K for separation. The requirement of mass resolving power increases linearly with mass.

Figure 7:
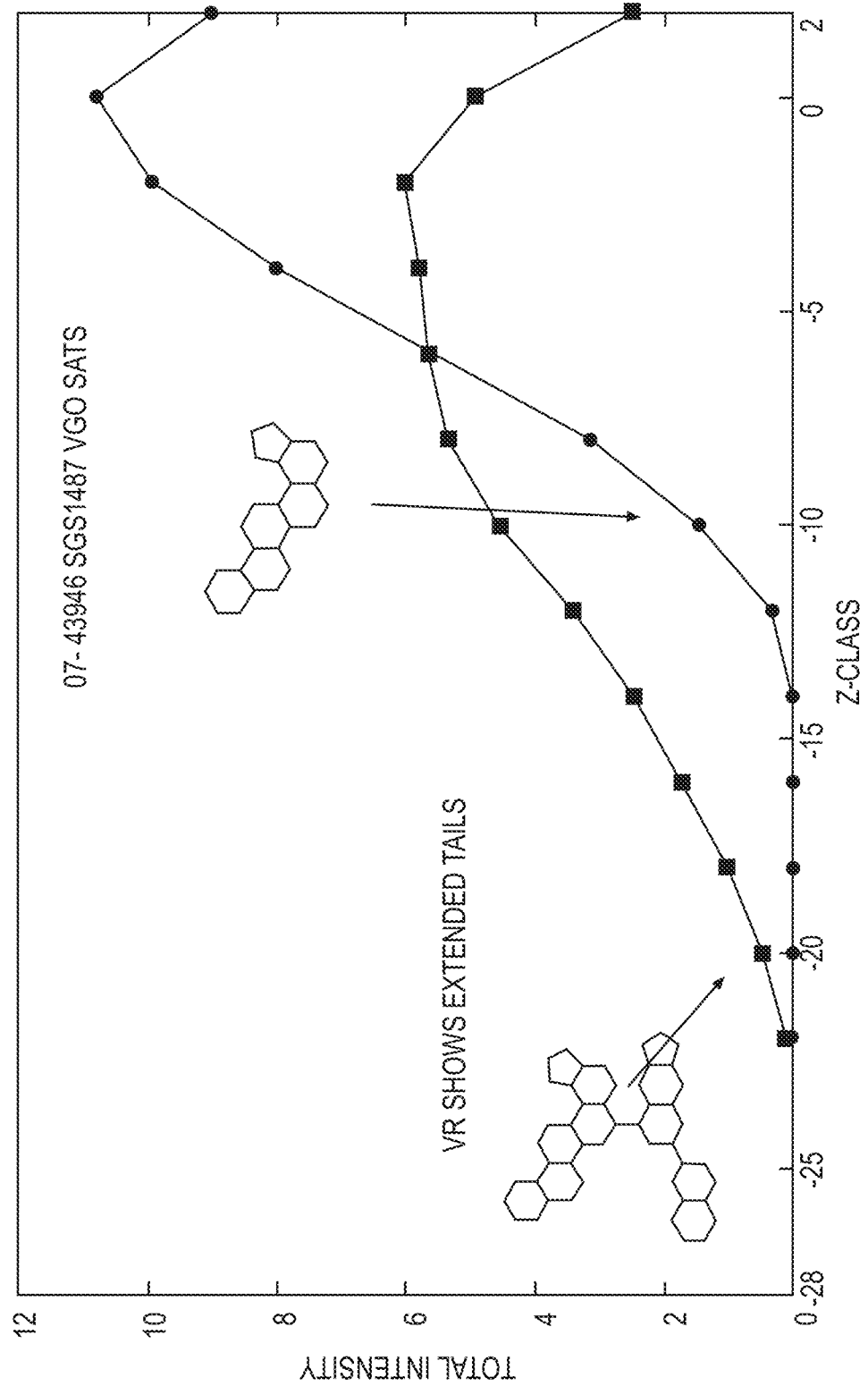
FIG. 7 shows Z-number distributions for saturates of VR and vacuum gas oil (VGO).

In addition to alkyl saturates, laser desorption ionization with FTICR-MS is also effective for characterizing saturates with one or more naphthenic rings. FIG. 7 shows the Z-number distribution (intensity values) from a mass spectra of a saturates portion derived from both a vacuum resid sample and a vacuum gas oil sample. Z is the hydrogen deficiency value as in $C_cH_{2c+Z}$. Non-cyclic alkanes or paraffins have Z number of 2. 1-ring cycloalkanes have Z number of 0. 6-ring cyclic alkanes have a Z-number of −10. For the vacuum gas oil saturates portion, Z-numbers ranging from 2 to −12 (0 to 7 naphthenic rings) were observed, which is largely consistent with the results from traditional hydrocarbon analysis. For the vacuum resid saturates portion, Z-numbers ranging from 2 to −24 (0 to 12 naphthenic rings) were observed. FIG. 7 compares the Z-distribution for the vacuum gas oil and vacuum resid saturates portions. Since olefin and aromatic contents in the saturates portions are very low, the large Z-number is believed to correspond to multi-naphthenic core structures, such as alkyl bridged polynaphthenes.

Figure 8:
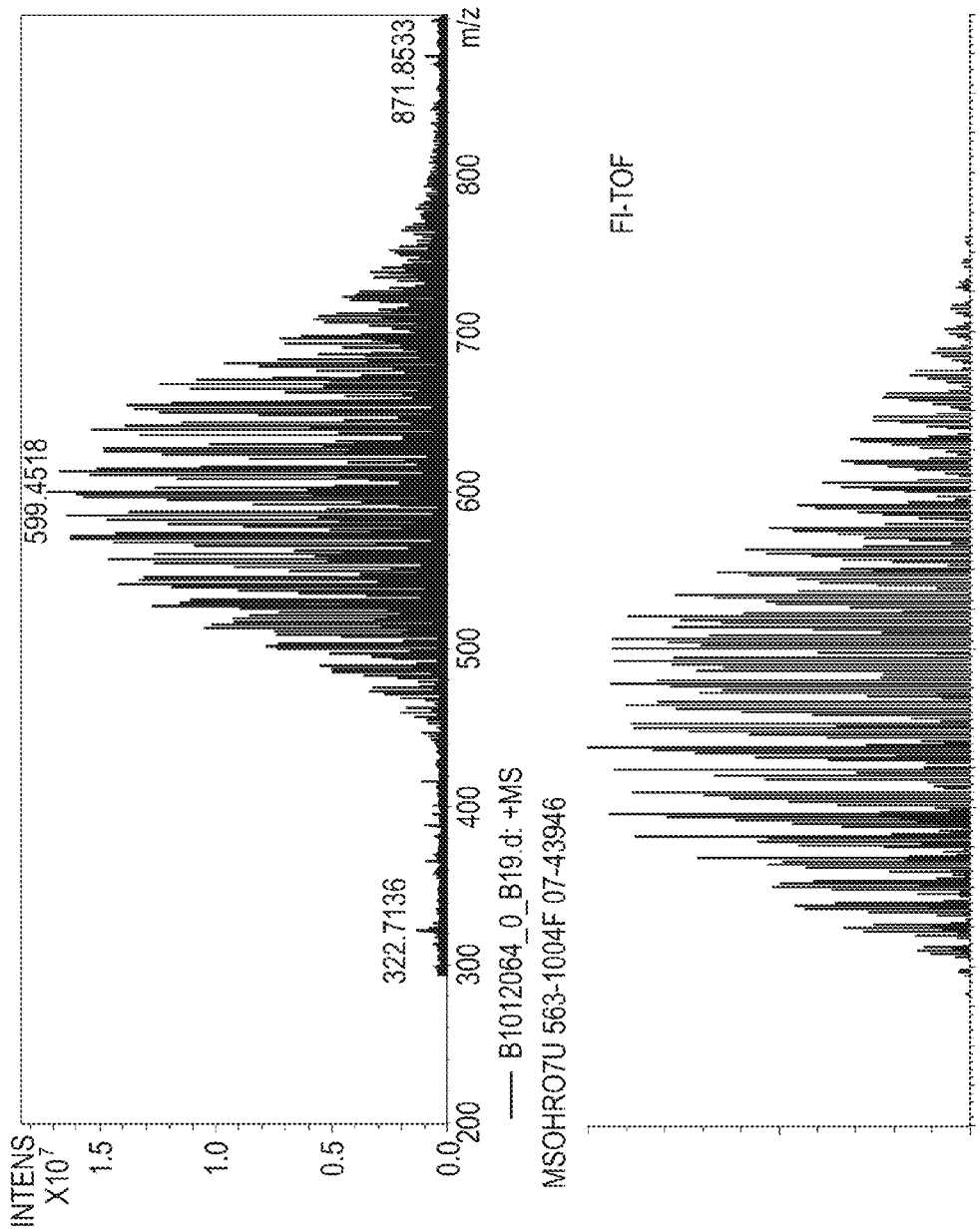
FIG. 8 shows a comparison of two types of ionization techniques for generating mass spectra of VGO saturates. (Top: LDI-Ag MS, Bottom: GC-FI-TOF MS)

Although an LDI-Ag technique allows for more detailed characterization of saturates, the method appears to be less effective for samples containing compounds with molecular weights below 400 Daltons. FIG. 8 shows a comparison of laser desorption ionization FTICR MS and field ionization time-of-flight MS for a vacuum gas oil sample, where more than 10 wt % of the sample corresponds to compounds with a molecular weight below 400 Daltons. Once again, the top spectrum is shifted to account for the mass of the silver ions in the laser desorption ionization technique. However, in FIG. 8 the top and bottom spectra are not similar in shape. The LDI-Ag technique appears to be less effective for forming ion adducts of compounds with a molecular weight of about 400 Daltons or less. As a result, these lighter compounds are not represented in the proper proportion in the laser desorption ionization spectrum of the sample in FIG. 8. Based on the reduced representation of lighter compounds in the mass spectrum generated by laser desorption ionization, it is preferable to use laser desorption ionization FTICR MS for saturate samples containing less than 10 wt % of compounds with a molecular weight of 400 Daltons or less, such as samples containing less than 5 wt % of compounds with a molecular weight of 400 Daltons or less. Because molecular weight is correlated with boiling point, selection of a sample with a higher boiling point is preferable for use in performing a laser desorption ionization FTICR MS characterization, such as a saturates sample or other sample with a T5 boiling point of at least 375° C. or at least 400° C.

Figure 9:
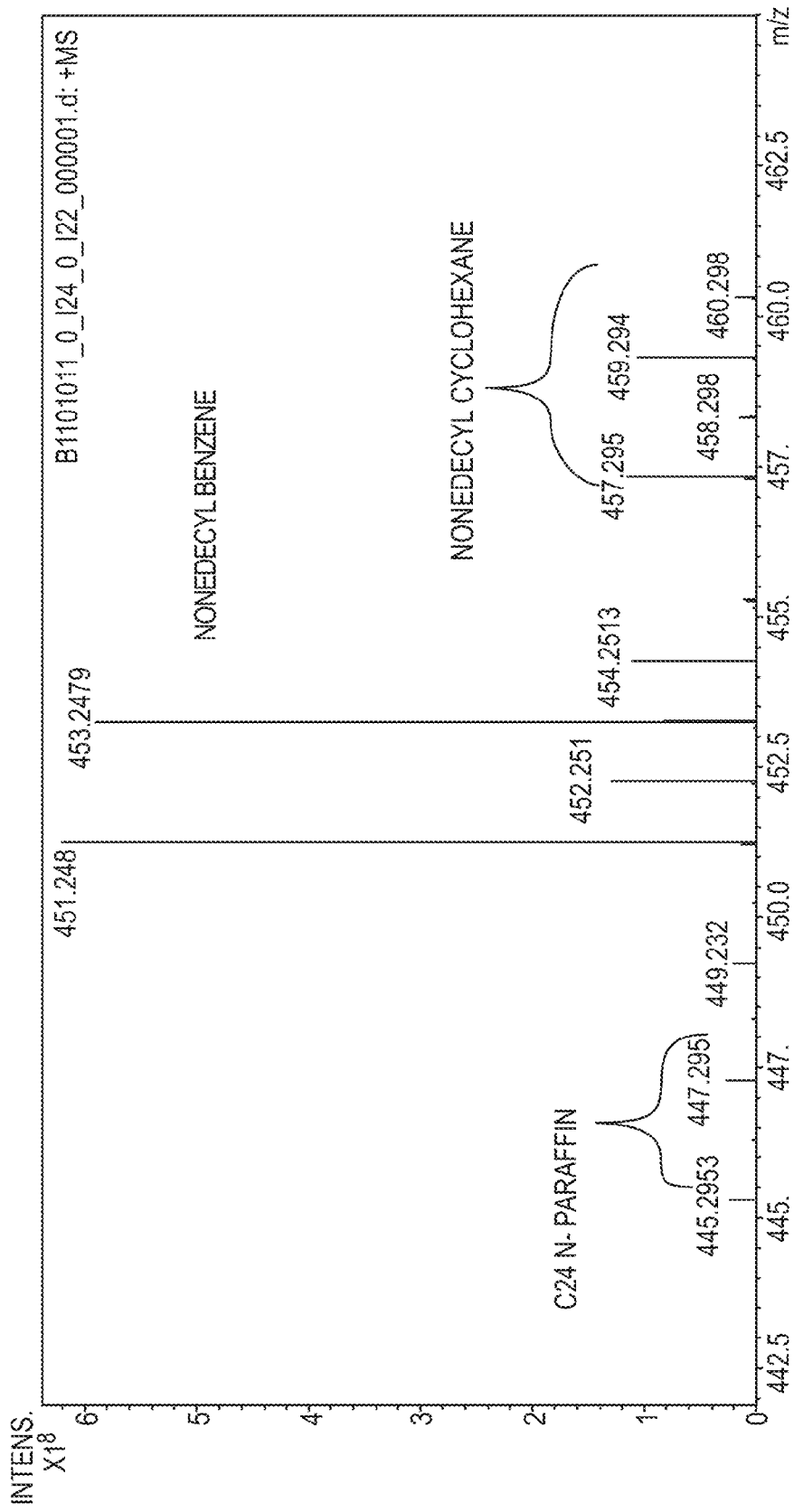
FIG. 9 shows examples of peak intensities for various types of compounds in a saturates sample.

Laser desorption ionization also appears to have different ionization capabilities for different types of compounds. FIG. 9 shows a laser desorption ionization FTICR MS spectrum for three types of compounds with similar molecular weights. The spectrum shows signal peaks corresponds to a $C_{24}$ n-paraffin (saturated alkane), nonedecylcyclohexane (a $C_{25}$ saturated naphthene), and nonedecyl benzene (a C25 aromatic). Comparable amounts of each of the compounds were used in an initial sample. As shown in FIG. 9, the peak intensity for the aromatics is much greater than the peak intensity for the saturate molecules. FIG. 9 shows that applying laser desorption ionization FTICR MS to a whole petroleum (crude oil) sample could pose difficulties, as aromatics would preferentially be detected. This would lead to errors in relative composition in the form of higher apparent aromatic contents and lower apparent saturate contents.

To a lesser extent, the naphthene in FIG. 9 also shows a larger peak intensity than the peak intensity for the paraffin molecule. To account for this, a response factor or weighting factor may be needed to adjust for the difference in how readily different types of saturates form ion adducts.

Overview—Model of Composition

Based on the above, laser desorption ionization with high resolution mass spectrometry (such as FTICR-MS) can be used to characterize a saturates sample or a portion of a petroleum sample. The methods for characterizing a saturates sample as described above can be combined with other analytical techniques to develop a model of composition for a petroleum sample.

One option for characterizing a heavy hydrocarbon fraction is to construct a model of composition for the fraction. A model of composition is based on the individual compounds within a fraction, but allows the compounds to be categorized and/or grouped in a manner that allows for more meaningful analysis of the composition. For example, petroleum oils and high-boiling petroleum oil fractions often include many members of a homologous series of hydrocarbons. One example of a homologous series is a series of hydrocarbons that differ only by the presence or absence of one or more $CH_2$ groups in an alkyl chain in the hydrocarbons. The alkyl chains can be side chains or the main chains of the similar or homologous molecules. Characterizing the compounds in a model based on homologous molecule types allows a complex composition to be expressed in a more usable manner, while still retaining a large portion of the underlying information in the full composition.

One of the difficulties in constructing a model of composition for a heavy hydrocarbon sample is that no single spectroscopic technique allows for detailed gathering of information for all portions of a sample. Even for mass spectrometry, a variety of techniques are required in order to create ions in a controlled manner for eventual detection by a mass spectrometer. In particular, due to the large number of compounds already present within a heavy hydrocarbon sample, it is desirable to select ionization techniques that do not result in formation of fragments and/or that otherwise substantially add to the number of peaks present in a mass spectrum. Thus, ionization methods that are characterized as "soft" methods that reduce or minimize fragmentation during ion formation are generally preferred.

By using various soft ionization techniques, the relative amounts of compounds within a composition group can be determined. The overall weight percent for each composition group can also be determined by other methods, such as conventional mass analysis after separation of a sample into composition groups. The relative amounts within each composition group can then be scaled based on the weight percentage for each composition group to develop an overall model of composition. Optionally, the model of composition can be further refined based on other measurements. For example, the sulfur content of the total sample and/or the sulfur content of one or more of the compositional groups can be determined After scaling the compositional groups based on the weight percentages, the sulfur amount for a compositional group and/or the total composition based on the model of composition can be compared with the measured values. If the values do not match, the model of composition can be refined to more closely match the measured values.

In a preferred embodiment, one or multiple soft ionization methods are used to generate molecular ions or pseudo molecular ions for petroleum molecules of different polarities and classes. Pseudo molecular ions include protonated ions, deprotonated ions, or cation or anion adducts of a parent molecule of the heavy petroleum or hydrocarbon sample. It is noted that formation of pseudo-molecular ions is explicitly included in the definition of ionizing a sample for measurement via mass spectrometry.

Typical Flow of Generating Model-of-Composition

The following describes a work process to generate a model-of-composition for petroleum using high resolution mass spectrometry. First, one or more separations are performed to separate compounds within a petroleum or heavy hydrocarbon sample into like species, molecular lumps, or composition groups. For example, a heavy hydrocarbon sample can initially separated into an asphaltenes portion and a deasphalted oil portion using a solvent deasphalting process. The deasphalted oil can then be separated into various types of composition groups, including saturates, aromatics, sulfides and polars. More than one composition group of a given type can be formed during separation, such as multiple composition groups corresponding to different aromatic ring classes. In a preferred embodiment, aromatics are separated into a plurality of aromatic ring classes (ARC), such as 1—Ring Aromatics (ARC1), 2—Ring Aromatics (ARC2), 3—Ring Aromatics (ARC3), and 4—Ring Aromatics Plus (ARC4+) before mass spectrometric analysis. High pressure liquid chromatography is an example of a method that is suitable for separating the deasphalted oil into a plurality of composition groups.

Figure 10:
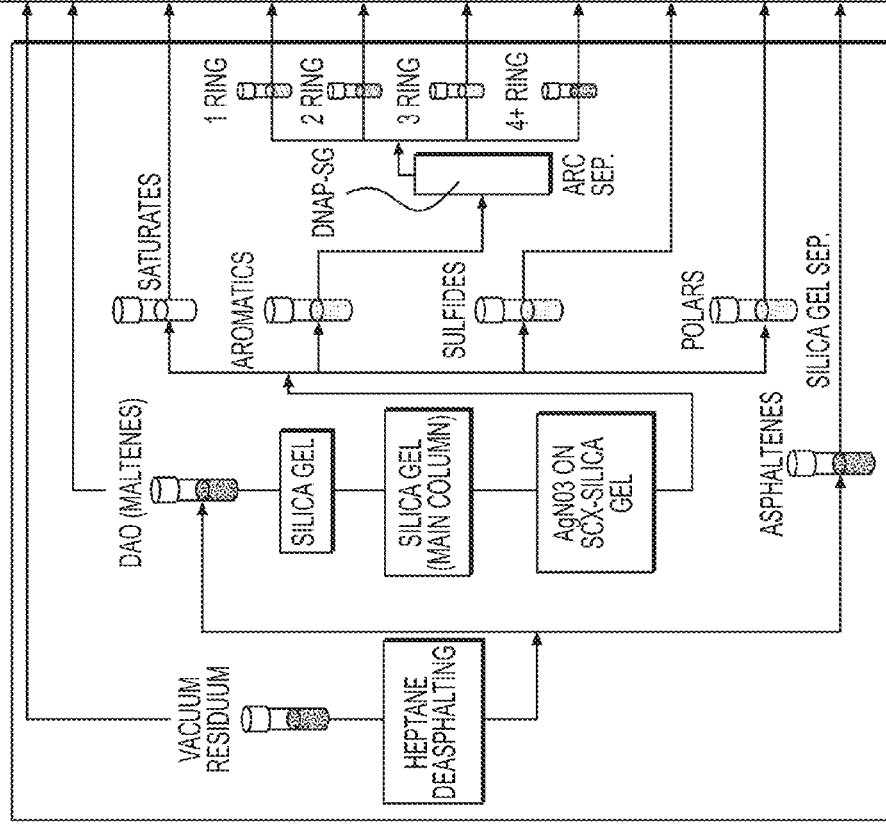
FIG. 10 schematically shows a process flow for creating a model of composition.

FIG. 10 shows an example of a process flow for creating a model of composition for a heavy hydrocarbon fraction. If the sample's initial boiling point is at or above 1000° F. (538° C.), solvent deasphalting is used to separate asphaltenes from the remainder of the sample. The remaining deasphalted oil (DAO) is further separated using a high-performance liquid-chromatographic (HPLC) technique. The fractions that elute from this HPLC technique include: saturates, aromatic-ring classes (ARC) 1-4, sulfides, and polars. Each of these fractions, including asphaltenes, can be analyzed by one or more of a variety of techniques, including: FTICR MS, field-desorption mass spectrometry (FDMS), nuclear magnetic resonance (NMR), elemental analysis, and other bulk properties.

APPI FTICR MS is used to estimate the distribution of chemical formulae within the ARC1-4, sulfides, and asphaltene fractions. The molecular composition of the polar fraction is known to be dominated by molecules containing basic nitrogen, and containing organic acid groups. Here, the distribution of chemical formulae is estimated by analyzing the DAO by NESI (negative ion ESI) FTICR MS, and by PESI (positive ion ESI) FTICR MS, then superimposing the two analyses. Laser desorption ionization FTICR MS is used to determine the molecular composition of the saturates fraction, and can optionally be used in place of APPI FTICR MS for asphaltenes (or other compounds that boil above 1300° F.). It is noted that a variety of soft ionization methods are used to generate the molecular ions or pseudo molecular ions for measurement using FTICR-MS. The soft ionization methods include, for example, matrix assisted laser desorption ionization to ionize saturate molecules; APPI/APCI to ionize aromatic petroleum molecules; positive ion ESI (PEST) to ionize basic nitrogen molecules; negative ion ESI (NEST) to ionize acidic molecules; and laser desorption ionization or matrix assisted laser desorption to ionize high boiling molecules (such as molecules that boil above 1300° F.).

After obtaining the FTICR-MS data for the various composition groups, a full composition is assembled by combining the composition data. Preferably, the composition groups are weighted based on a weight percentage for the corresponding composition group in a sample. After separating composition groups by liquid chromatography or another technique, the weight percentage for each composition group can be determined by any convenient method. The resulting model of composition is then preferably reconciled with other analytical data, such as a) Field Desorption MS for Molecular Weight (MW) distribution; b) Bulk properties such as elemental composition, high temperature simulated distillation (HT-SIMDIS), microcarbon residue (MCR) or conradson carbon (CCR) residue; c) Average structures by NMR, such as % Aromatic carbon (Ca), average aromatic cluster size (C#), amount of C in long chains, or degree of chain branching; and d) Heteroatom types by X-ray Photoelectron Spectroscopy (XPS), such as organic forms of sulfur, or pyrrolic, pyridinic and quaternary nitrogens.

Soft Ionization of Non-Saturates by APPI

The following is an example of how soft ionization of a sample or a portion of a sample (such as a composition group separated out using HPLC) can be performed using APPI. For the soft ionizations described herein that were performed using APPI, typically about 4 mg of a petroleum (i.e., heavy hydrocarbon) sample was dissolved in 20 ml of toluene to form a 200 ppm solution. The solution was introduced into the APPI source using a Cole-Palmer syringe pump and a 250 µl syringe. The flow rate was normally controlled at 120 µl/hr. The source was manufactured by Syagen and comprised of a heated capillary needle and Krypton UV lamp with ionization energy of 10.6 eV. Nitrogen was used for both nebulizing gas and drying gas. Nebulizing gas flow rate was normally between 1 to 3 L/min while drying gas flow rate was normally between 2 to 7 L/min. The flow rates were adjusted to maximize APPI-FTICR signals. For some of the measurements, nebulizing gas temperatures were varied from 350° C. to 450° C. For characterization of vacuum resid, 450° C. was generally used in order to maximize the signal of high boiling molecules. Toluene is used as both solvent and chemical ionization agent. Thermal chemistry was not observed during APPI for ionization. This is believed to be mainly due to the short residence time of the sample ions.

Figure 11:
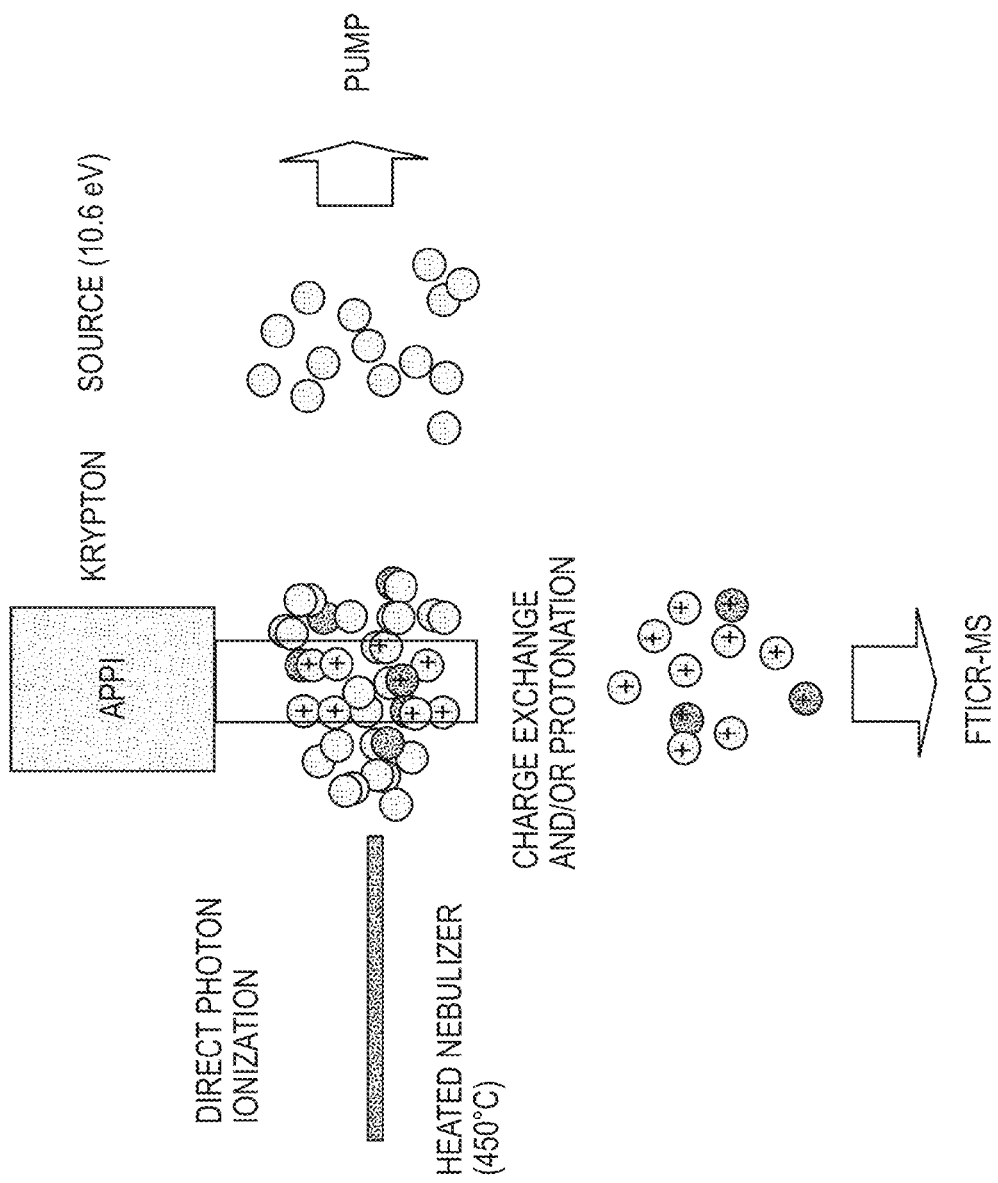
FIG. 11 schematically shows the basic principles of APPI for ionization of a sample.

FIG. 11 demonstrates the basic principles of APPI. The sample solution is dispersed into fine droplets and vaporized by co-spraying with a nebulizing gas through a heated stainless needle. The sample molecules are further desolvated by a counter flow of drying gas. The gas phase solvent and analyte molecules are ionized via UV photoionization. Since analyte molecules are present in a much lower level (200 ppm), the gas phase contains primarily solvent molecules. Consequently, direct photoionization produces mostly solvent molecule ions and very few analyte ions. The latter are mostly ionized by secondary ion-molecule reactions in the source region. In the current applications, toluene is used as solvent as it can dissolve most of the sample types including asphaltenes. Toluene has an ionization potential (IP) of 8.8 eV and can be directly ionized by a Krypton photon source (10.6 eV). On the other hand, the IP of toluene is higher than that of most aromatic molecules. (Benzene, with an ionization potential of 9.2 eV, is one of the few exceptions.) The toluene molecular ions react with analyte molecules via ion-neutral collisions. For most aromatic molecules, electron transfer will take place by first ionizing a toluene molecule, followed by subsequent ionization of a target molecule during a collision between the target molecule and the ionized toluene. For almost all aromatic molecules, this method of energy deposition is sufficiently low that target (analyte) molecular ions are formed without fragmentation. This soft ionization is important for VR analyses due to the complexity of the sample compositions. Low levels of protonation have been observed for low molecular weight polar molecules. Protonation can be pronounced when more polar solvents (such as methanol and acetonitrile) are used.

Soft Ionization of Polars by ESI

The following is an example of how soft ionization of a sample or a portion of a sample (such as a composition group separated out using HPLC) can be performed using ESI. For the soft ionizations described herein that were performed using ESI, optimal sample concentrations depend on nitrogen and acid levels. In a typical positive ion ESI, about 20 mg of a sample was first dissolved in 20 ml toluene. 3 ml of the solution was diluted with 17 ml of a toluene/ACN mixture (15% toluene). The final analyte concentration was about 150 ppm. The final toluene concentration was about 30%. 20 to 100 µl of formic acid was added to the solution to promote liquid conductivity. The electrospray current was maintained at greater than 10 µA to maintain spray stability. In a typical ESI in negative ion mode, about 20 mg of VR sample was first dissolved in 20 ml toluene. 3 ml of the solution was diluted with 17 ml of toluene/methanol mixture (15% toluene). The final sample concentration was about 150 ppm. 20 to 100 µl of $NH_4OH$ was added to promote liquid conductivity and achieve desired electrospray current of >10 µA. The liquid sample was delivered into ESI source by a syringe pump with a flow rate of 120 µl/hour. Nitrogen was used for both nebulizing and dryer gases. The nebulizing temperature was ambient and the drying gas temperature was set at 200° C.

It is generally believed that positive ion ESI (PESI) selectively ionizes basic nitrogen compounds via protonation while negative ion ESI (NEST) selectively ionizes acids, phenols and non-basic nitrogen compounds via de-protonation. In ESI, a large potential of approximately 2,000 to 4,000 V is applied to a capillary needle through which a sample solution containing electrolyte (e.g. formic acid for positive ion or $NH_4OH$ for negative ion) are introduced. A counter electrode is maintained at 0 V, thus creating a strong electric field between it and the capillary. The electric field permeates the solution at the capillary needle tip and causes separation of the ions in solution. In positive ion conditions, negative ions move toward the center of the capillary whereas positive ions are enriched at the surface of the liquid at the capillary tip. The repulsion of the excess charges at the surface and the pull of the electric field form a "Taylor cone" at the tip of capillary. As the charge repulsion overcomes the surface tension of the liquid, a fine spray of charged droplets is created. As those droplets pass through a heated capillary within the mass spectrometer, the solvent evaporates, increasing the surface charge density. Coulombic repulsion causes droplets to fission into successively smaller daughter droplets, resulting in the eventual removal of all solvent molecules to yield unhydrated gas-phase ions (charge residual model) or direct ejection of ions into gas phase (ion evaporation model).

For ESI applications in petroleum, solvents are normally binary mixtures containing both petroleum-friendly solvent and ESI-friendly solvent, such as toluene/acetonitrile (positive ion mode) or toluene/methanol (negative ion mode). For VGO samples, toluene content can be as low as 5% without significant sample precipitation. For VR DAOs and asphaltenes, we have observed large solid precipitation using the conventional mix adopted for VGO analysis. All VR samples are soluble in 100% toluene. However, toluene does not spray under the ESI conditions. To obtain a steady ESI current, a maximal 50% toluene may be used.

A uniform response factor is assumed for ESI although it is understood that there are significant variations in positive ion ESI responses for various nitrogen compound types. In negative ion ESI of acids, the uniform response assumption is not far from reality. Previous research has shown that TAN measurements based on stearic acid match well with that of titration of total acids. Similar to APPI applications, FTICR is mainly used to provide Z-distribution of homologues and heteroatom distribution of polar species in petroleum samples. The nitrogen concentrations can be normalized to elemental nitrogen and acids can be normalized to the TAN measurements. Positive and negative ion ESI can be used to detect bases and acids in VR. These molecules are then used to construct basic nitrogen and acid compositions.

Figure 12:
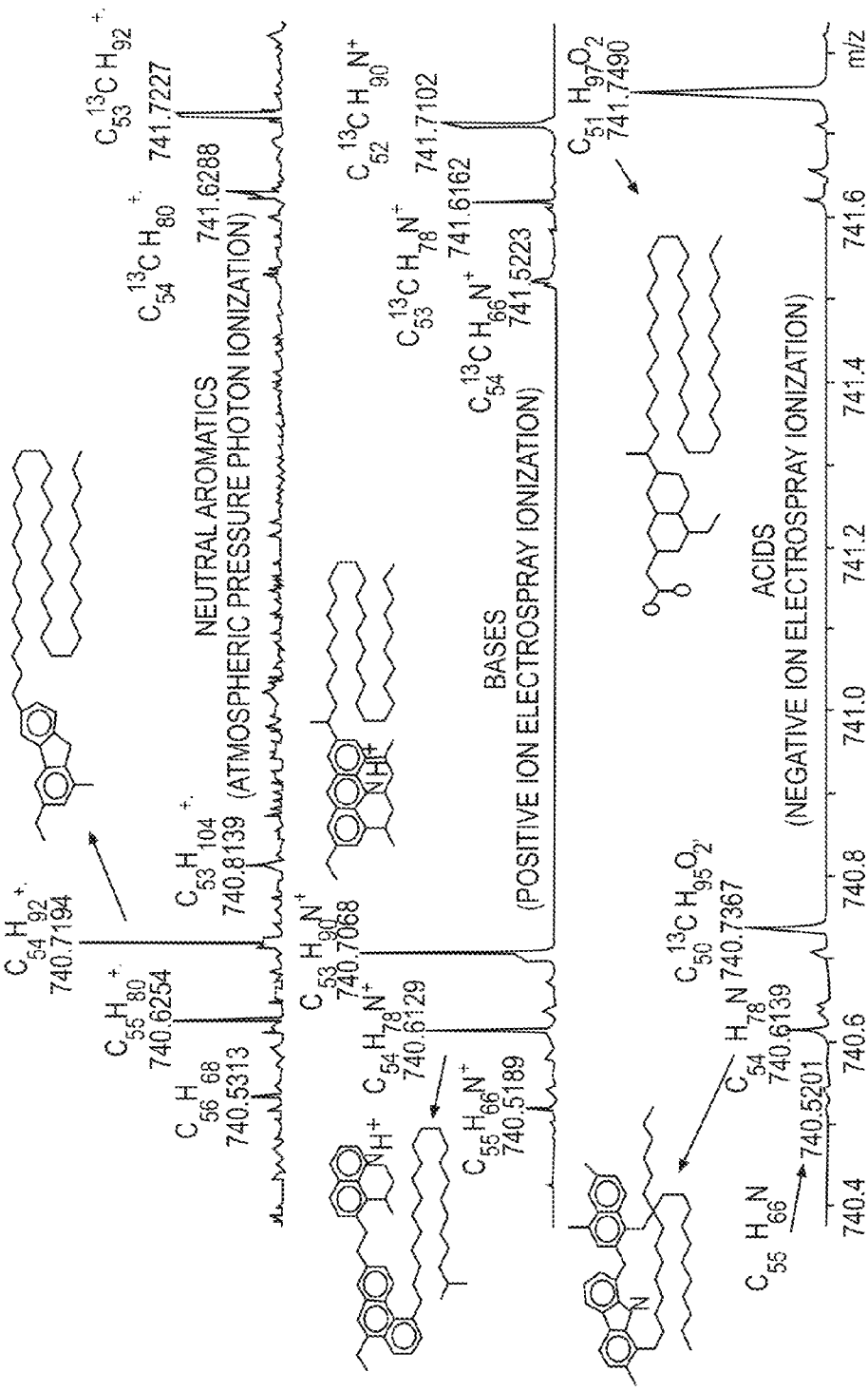
FIG. 12 shows examples of using multiple ionization methods to characterize a sample.
Figure 13:
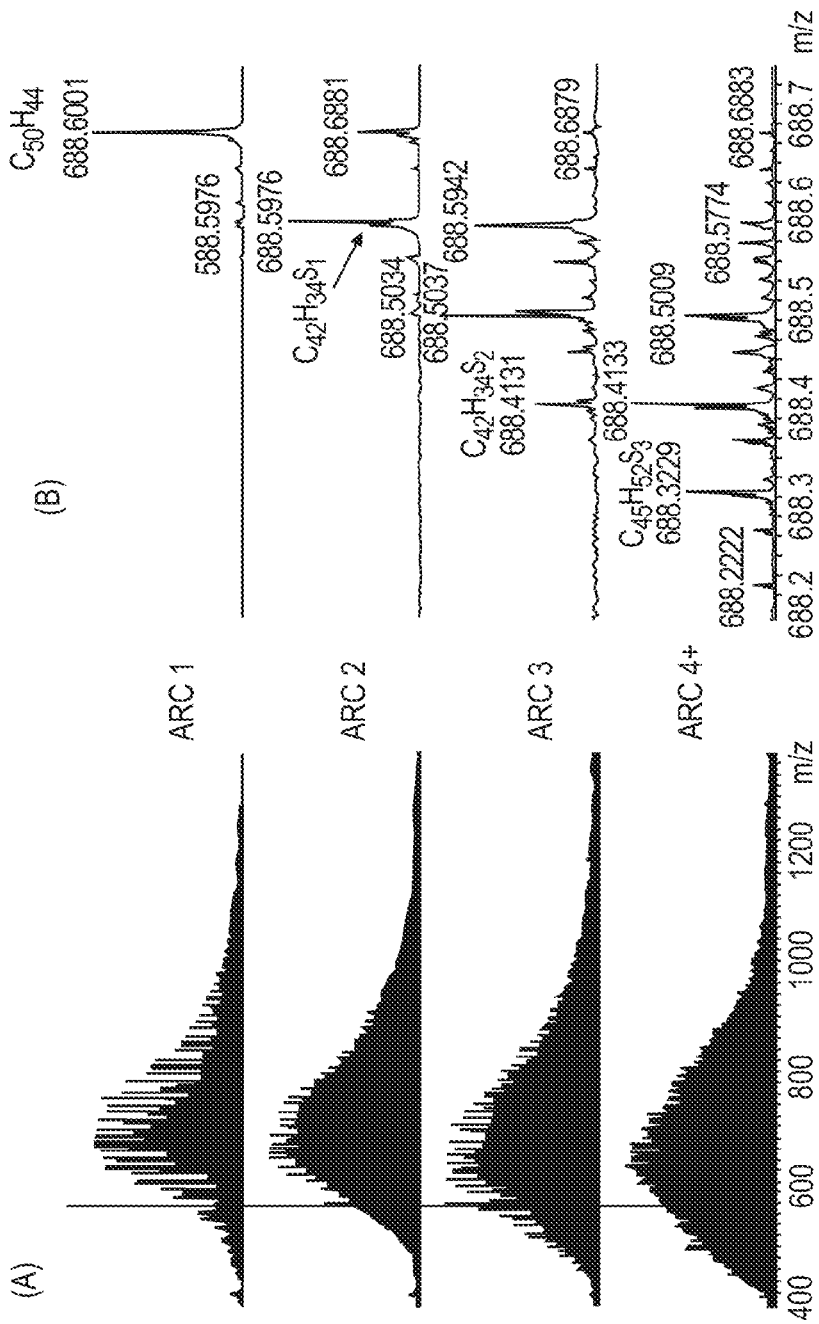
FIG. 13 shows examples of mass spectra corresponding to various ring classes.
Figure 14:
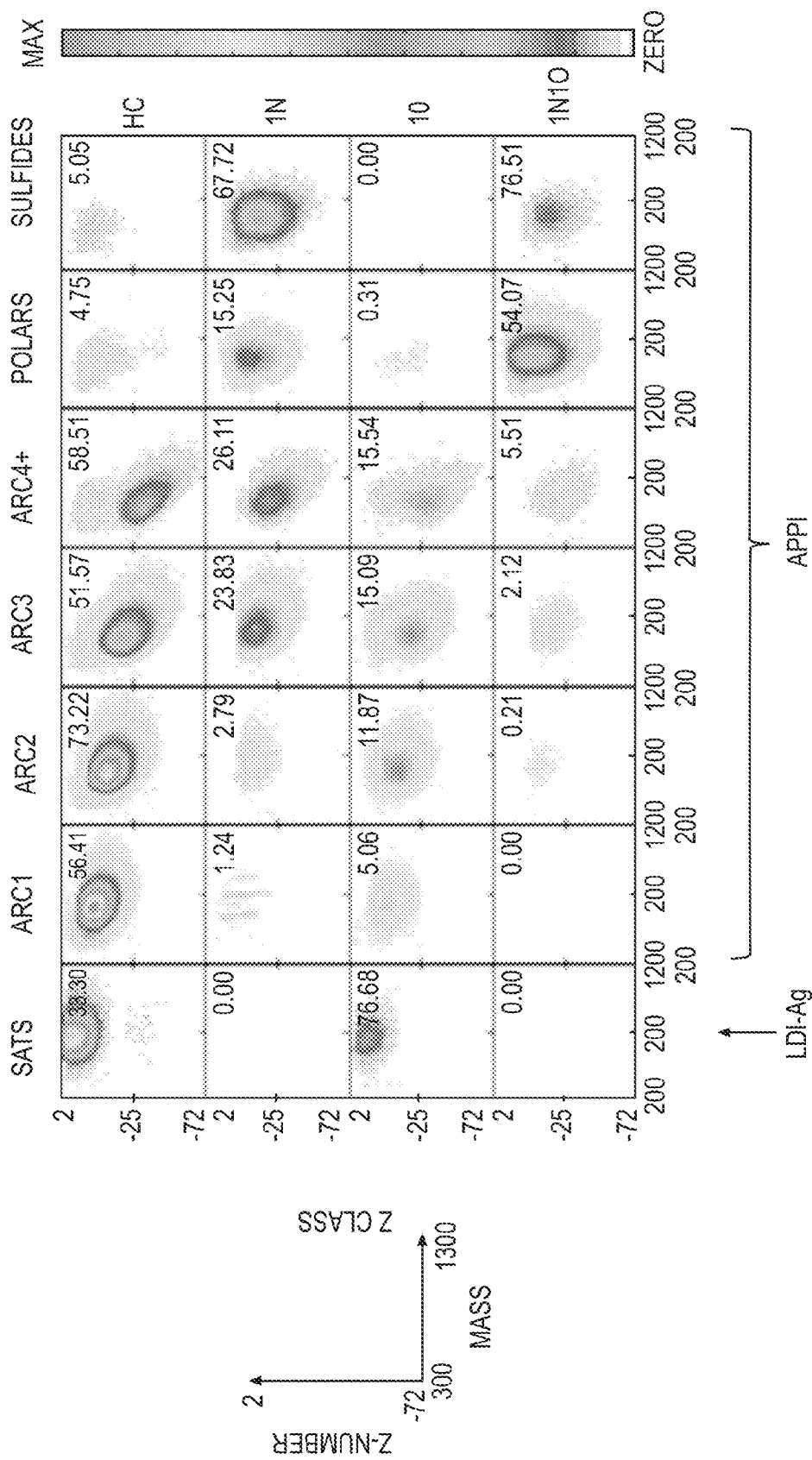
FIG. 14 shows an example of output generated by an FTICR mass spectrometer. Saturates data is generated by LDI-AG while data of other fractions were generated by APPI.

FIG. 12 shows the use of multiple ionization methods to generate molecular ions for neutrals, bases and acids by APPI, PESI and NESI, respectively. FIG. 13 shows the mass spectra of aromatic ring classes by APPI. FIG. 14 shows an image plot of Z-number and molecular weight distribution of various chemical and solubility fractions where a majority of fractions are analyzed by APPI-FTICR MS and saturates fraction is analyzed by LDI-Ag FTICR MS. The plot shows smooth transitions in composition from saturates to arc1, arc2, arc3 and arc4 fractions. LDI-Ag method filled an important gap in composition modeling of whole heavy oil.

Assemble-Full Composition and Reconcile to Key Analytical Targets

The chemical formulae distribution determined by FTICR MS analysis of the separated fractions detailed above can be reconciled with the other analyses within the advanced analytical protocol shown in FIG. 10. For example, each composition group's FTICR MS analysis can be extrapolated to higher molecular weights, and lower hydrogen deficiency classes (Z-number), to match the molecular weight distribution predicted by FDMS analysis (or another technique with lower resolution for individual compounds). The total abundance of elements in each fraction, e.g. carbon, hydrogen, sulfur, nitrogen, oxygen, nickel, and vanadium, as predicted from the FTICR MS-derived chemical formulae can also be reconciled to that measured by elemental analysis. This reconciliation is preferably done using the constrained entropy maximization procedure. Reconciliation to high-temperature is feasible through use of appropriate property targets in the above procedure, and through the use of a correlation that relates boiling point temperatures to chemical formulae. Assignment of molecular (e.g. structure oriented lumping (SOL)) lumps to each chemical formula is aided by other measured properties, e.g. microcarbon residue, NMR, and heteroatom types identified by X-ray Photoelectron Spectroscopy (XPS).

In an embodiment, the reconciliation process includes blending the FTICR-MS data by fraction weight for each compositional group, then autotuning to satisfy property constraints. These property constraints can include: compositional group weight, and weight percent of hydrogen, sulfur, nitrogen, nickel and vanadium both overall and within each compositional group where there is available data.

Elemental properties of selected compositional groups or fractions used as inputs include: hydrogen, sulfur, nitrogen, nickel and vanadium content. Hydrogen contents of asphaltenes and of the following DAO compositional groups or fractions are measured by combustion (ASTM D 5291): saturates, aromatics, sulfides, and polars. Nitrogen content of asphaltenes, and the aromatics, sulfides, and polar fractions of the DAO are also measured using the ASTM D 5291 technique. At present, the sulfur content of all compositional groups or fractions, except DAO saturates, are measured by ASTM D 2622 X-ray fluorescence. Nickel and vanadium content, among other metals, is typically measured on the total resid, asphaltene, and DAO fractions using the ASTM D 5708 technique.

Additional Embodiments

Embodiment 1

A method for characterizing a hydrocarbon sample, comprising: obtaining a hydrocarbon sample comprising at least about 90 wt % of saturate compounds; forming saturate-ion adducts by laser desorption ionization in the presence of a soft Lewis acid; detecting the saturate-ion adducts using mass spectrometry with a resolving power of at least about 10,000, the detected saturate-ion adducts comprising a mass spectrum which is a list of accurate masses and intensities of the corresponding masses; selecting the detected saturate-ion adducts based on Kendrick mass defect values so that Kendrick mass defect values of between about 0.150 to about 0.400 are retained; assigning molecular formula to the selected saturate-ion adducts in the mass spectrum; and determining weight percentages for compounds in the petroleum or hydrocarbon sample based on the intensities of the saturate-ion adducts.

Embodiment 2

The method of Embodiment 1, wherein obtaining a hydrocarbon sample comprising at least about 90 wt % of saturate compounds comprises separating a petroleum sample by liquid chromatography.

Embodiment 3

The method of any of the above embodiments, wherein the hydrocarbon sample contains less than 10 wt % of saturate compounds with a mass of 400 Da or less.

Embodiment 4

The method of any of the above embodiments, wherein the saturate-ion adducts are detected using Fourier transform ion cyclotron resonance (FTICR) mass spectrometry.

Embodiment 5

The method of any of the above embodiments, wherein forming the saturate-ion adducts in by laser desorption ionization further comprises forming the saturate-ion adducts in the presence of a matrix material, the matrix material preferably comprising at least one of a metal powder and an organic acid, the metal powder preferably being a cobalt powder with a particle size of 30 µm, the organic acid preferably being 2,5-dihydroxy benzoic acid.

Embodiment 6

The method of any of the above embodiments, wherein the detected saturate-ion adducts are retained if their Kendrick mass defect values of about 0.200 to about 0.300.

Embodiment 7

The method of any of the above embodiments, wherein assigning molecular formula to the detected saturate-ion adducts comprises assigning molecular structures containing only C, H, N, S, O, and Ag atoms, wherein the number of N atoms in an assigned molecular structure is 4 or less, the number of S atoms in an assigned molecular structure is 4 or less, the number of O atoms in an assigned molecular structure is 4 or less, and the number of Ag atoms in an assigned molecular structure is 2 or less.

Embodiment 8

The method of any of the above embodiments, further comprising grouping the filtered saturate-ion adducts based on at least one of a number of heteroatoms, a Z-class, and the detected molecular weight.

Embodiment 9

The method of any of the above embodiments, wherein the soft Lewis acid is at least one of $Ag^+$, $Au^+$, $Cu^+$, $Tl^+$, $Hg^+$, $Cs^+$, $Pd^{2+}$, $Cd^{2+}$, $Pt^{2+}$, $Hg^{2+}$, $CH_3Hg^+$, $Tl^{3+}$, and $Tl(CH_3)_3^+$, the soft Lewis acid preferably comprising $Ag^+$.

Embodiment 10

The method of any of the above embodiments, wherein the method for characterizing a hydrocarbon sample is used as part of a method for developing a model of composition for a heavy hydrocarbon sample, comprising: separating a heavy hydrocarbon sample having a T5 boiling point of at least about 350° C. to form a plurality of composition groups, including at least one saturates group; measuring a weight percentage for composition groups formed by separation of the heavy hydrocarbon sample; determining elemental formulas and relative amounts for compounds within separated composition groups using mass spectrometry, the ions for the mass spectrometry being formed using a soft ionization method; and calculating a model of composition for the heavy hydrocarbon sample based on the measured weight percentages for the composition groups, the determined elemental formulas for compounds within the separated composition groups, and the determined relative amounts for compounds within the separated composition groups, wherein the ions for the mass spectrometry of the at least one saturates group are formed using laser desorption ionization according to one of the above embodiments.

Embodiment 11

The method of Embodiment 10, further comprising adjusting the calculated model of composition by fitting the model of composition to one or more additional properties of the heavy hydrocarbon sample.

Embodiment 12

The method of Embodiment 11, wherein the one or more additional measured properties of the heavy hydrocarbon sample are selected from a total sulfur content, a sulfur content for a compositional group, a total nitrogen content, a nitrogen content for a compositional group, a total aromatics content, an aromatics content for a compositional group, a hydrogen to carbon ratio for the heavy hydrocarbon sample, or a hydrogen to carbon ratio for a compositional group.

Embodiment 13

The method of Embodiment 11 or 12, wherein at least one of the heavy hydrocarbon sample and the at least one saturates group has an initial boiling point of at least about 400° C.

Embodiment 14

The method of any of Embodiments 11 to 13, wherein less than about 5 wt % of the heavy hydrocarbon sample and/or less than about 5 wt % of the at least one saturates composition group comprises compounds with a molecular weight of less than 400 Daltons.

Embodiment 15

The method of any of Embodiments 11 to 14, wherein separating the heavy hydrocarbon sample comprises deasphalting the heavy hydrocarbon sample to form an asphaltenes composition group and a deasphalted oil, and separating the deasphalted oil to form the at least one saturates composition group, the at least one aromatics composition group, and the at least one polar composition group.

What is claimed is:

1. A method for developing a model of composition for a heavy hydrocarbon sample, comprising:
    separating a heavy hydrocarbon sample having a T5 boiling point of at least about 350° C. to form a plurality of composition groups, including at least one saturates group;
    measuring a weight percentage for composition groups formed by separation of the heavy hydrocarbon sample;
    determining elemental formulas, structures, and relative amounts for compounds within separated composition groups using mass spectrometry, wherein the structures determined for compounds within the at least one saturates group are 0-12 naphthene ring structures, the ions for the mass spectrometry being formed using a soft ionization method; and
    calculating a model of composition for the heavy hydrocarbon sample based on the measured weight percentages for the composition groups, the determined elemental formulas for compounds within the separated composition groups, and the determined relative amounts for compounds within the separated composition groups,
    wherein the ions for the mass spectrometry of the at least one saturates group are formed using laser desorption ionization;

directly measuring molecular weight distribution, bulk properties, average structures, and heteroatom types;

adjusting the calculated model of composition to match the properties directly measured to obtain an adjusted model of composition.

2. The method of claim 1, wherein at least one of the heavy hydrocarbon sample and the at least one saturates group has an initial boiling point of at least about 400° C.

3. The method of claim 1, wherein less than about 5 wt % of the heavy hydrocarbon sample comprises compounds with a molecular weight of less than 400 Daltons.

4. The method of claim 1, wherein less than about 5 wt % of the at least one saturates composition group comprises compounds with a molecular weight of less than 400 Daltons.

5. The method of claim 1, wherein separating the heavy hydrocarbon sample comprises deasphalting the heavy hydrocarbon sample to form an asphaltenes composition group and a deasphalted oil, and separating the deasphalted oil to form the at least one saturates composition group, the at least one aromatics composition group, at least one sulfide composition group, and the at least one polar composition group.

6. The method of claim 1, wherein directly measuring molecular weight distribution comprises using field desorption mass spectrometry.

7. The method of claim 1, wherein directly measuring bulk properties comprises measuring at least one of elemental composition by elemental analysis, boiling point by high temperature simulated distillation, and microcarbon residue or conradson carbon residue.

8. The method of claim 1, wherein directly measuring average structures comprises measuring at least one of % Aromatic carbon (Ca), average aromatic cluster size (C#), amount of C in long chains, and degree of chain branching by nuclear magnetic resonance.

9. The method of claim 1, wherein directly measuring heteroatom types comprises using X-ray Photoelectron Spectroscopy.

* * * * *